(12) United States Patent
Dalal et al.

(10) Patent No.: US 7,722,592 B2
(45) Date of Patent: May 25, 2010

(54) NON-TACKY ADHESIVE FASTENING SYSTEM FOR USE IN CONSUMER PRODUCTS

(75) Inventors: Urmish Popatlal Dalal, Milford, OH (US); Robin Lynn McKiernan, Mason, OH (US); Mark James Kline, Okeana, OH (US); Wolfgang Edgar Huhn, Chieti (IT); Italo Corzani, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/324,486

(22) Filed: Jan. 3, 2006

(65) Prior Publication Data

US 2007/0156111 A1 Jul. 5, 2007

(51) Int. Cl.
*A61F 13/15* (2006.01)
*A61F 13/20* (2006.01)

(52) U.S. Cl. ...................... 604/394; 604/393
(58) Field of Classification Search .......... 604/386–391
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,515,595 A | 5/1985 | Kievit et al. | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,710,189 A | 12/1987 | Lash | |
| 4,795,454 A | 1/1989 | Dragoo | |
| 4,834,735 A | 5/1989 | Alemany et al. | |
| 4,846,815 A | 7/1989 | Scripps | |
| 4,888,231 A | 12/1989 | Angstadt | |
| 4,892,536 A | 1/1990 | DesMarais et al. | |
| 4,894,060 A * | 1/1990 | Nestegard ................... 604/391 |
| 4,940,464 A * | 7/1990 | Van Gompel et al. ....... 604/396 |
| 4,946,527 A * | 8/1990 | Battrell ....................... 156/60 |
| 4,990,147 A | 2/1991 | Freeland | |
| 5,037,416 A | 8/1991 | Allen et al. | |
| 5,050,742 A | 9/1991 | Muckenfuhs | |
| 5,054,619 A | 10/1991 | Muckenfuhs | |

(Continued)

FOREIGN PATENT DOCUMENTS

WO    WO 99/32005 A    7/1999

(Continued)

OTHER PUBLICATIONS

PCT Search Report, mailed Jun. 13, 2007, 5 pages.

*Primary Examiner*—Melanie J Hand
(74) *Attorney, Agent, or Firm*—Amy M. Foust; Richard L. Alexander; Eric T. Addington

(57) ABSTRACT

A non-tacky adhesive fastening system may comprise an engaging member having an engaging surface with a non-tacky adherent disposed thereon and a receiving member having a receiving surface with a non-tacky adherend disposed thereon. The non-tacky adherent may be pre-engaged to the non-tacky adherend. The non-tacky adhesive fastening system, after aging, exhibits a T-Peel of less than about 12 N/inch and is refastenable.

6 Claims, 26 Drawing Sheets

U.S. PATENT DOCUMENTS

| | | |
|---|---|---|
| 5,137,537 A | 8/1992 | Herron et al. |
| 5,147,345 A | 9/1992 | Young et al. |
| 5,151,092 A | 9/1992 | Buell et al. |
| 5,221,274 A | 6/1993 | Buell et al. |
| 5,260,345 A | 11/1993 | Desmarais et al. |
| 5,269,775 A | 12/1993 | Freeland et al. |
| 5,342,338 A | 8/1994 | Roe |
| 5,387,207 A | 2/1995 | Dyer et al. |
| 5,397,316 A | 3/1995 | Lavon et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,669,897 A | 9/1997 | Lavon et al. |
| 5,865,823 A | 2/1999 | Curro |
| 5,899,895 A | 5/1999 | Robles et al. |
| 5,934,470 A | 8/1999 | Bauer et al. |
| 6,004,306 A | 12/1999 | Robles et al. |
| 6,004,308 A | 12/1999 | Haddock |
| 6,013,589 A | 1/2000 | Desmarais et al. |
| 6,107,537 A | 8/2000 | Elder et al. |
| 6,120,487 A | 9/2000 | Ashton |
| 6,156,424 A * | 12/2000 | Taylor .................... 428/355 R |
| 6,432,098 B1 | 8/2002 | Kline et al. |
| 6,764,475 B1 | 7/2004 | Olson |
| 6,854,624 B2 * | 2/2005 | Vogt et al. .................... 223/37 |
| 2004/0162536 A1 | 8/2004 | Becker et al. |
| 2004/0167486 A1 | 8/2004 | Busam et al. |
| 2004/0180197 A1 | 9/2004 | Everaerts et al. |
| 2005/0106387 A1 * | 5/2005 | Ishikawa et al. ............ 428/354 |
| 2005/0177127 A1 | 8/2005 | Ashton et al. |

FOREIGN PATENT DOCUMENTS

| | | |
|---|---|---|
| WO | WO 2005/077313 A | 8/2005 |
| WO | WO 2005077313 A1 * | 8/2005 |

* cited by examiner

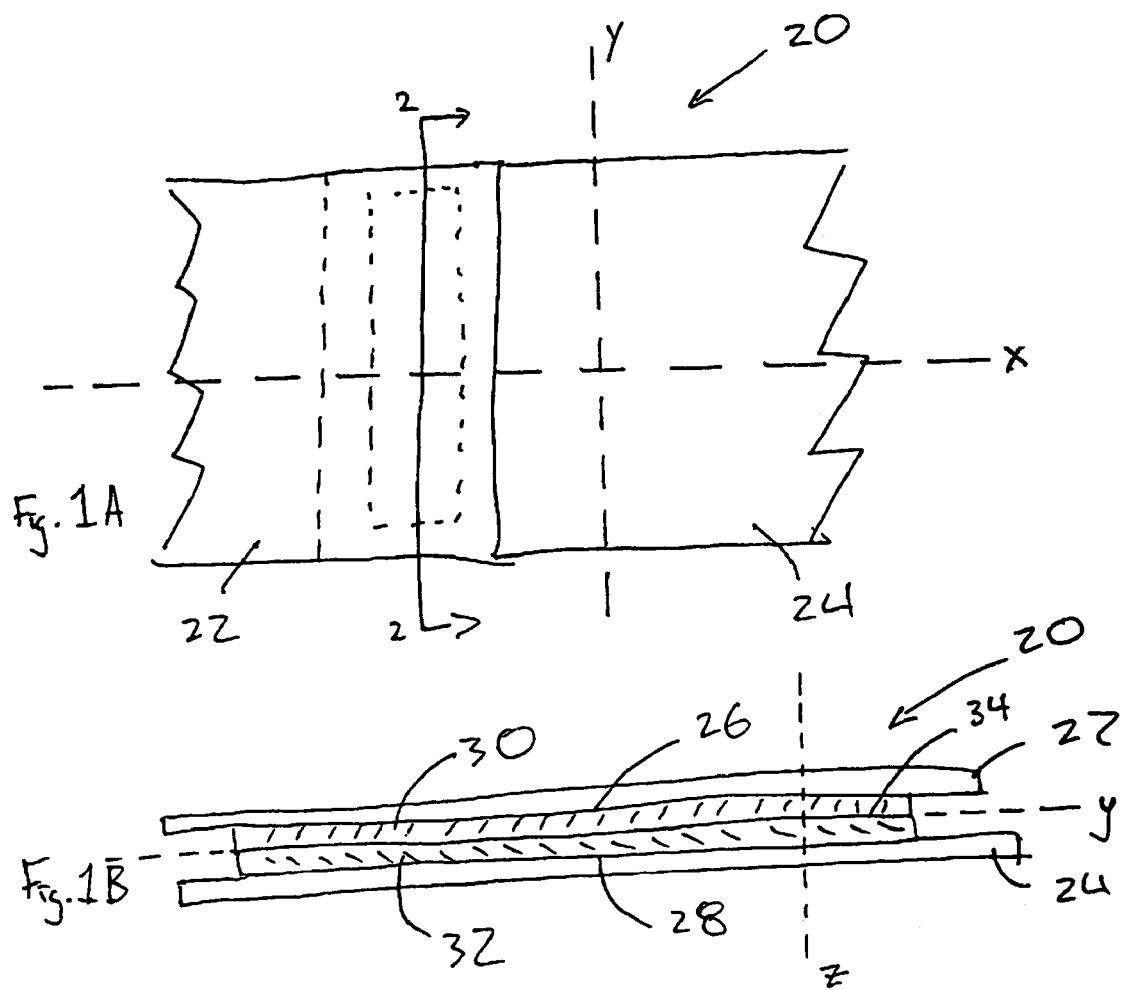

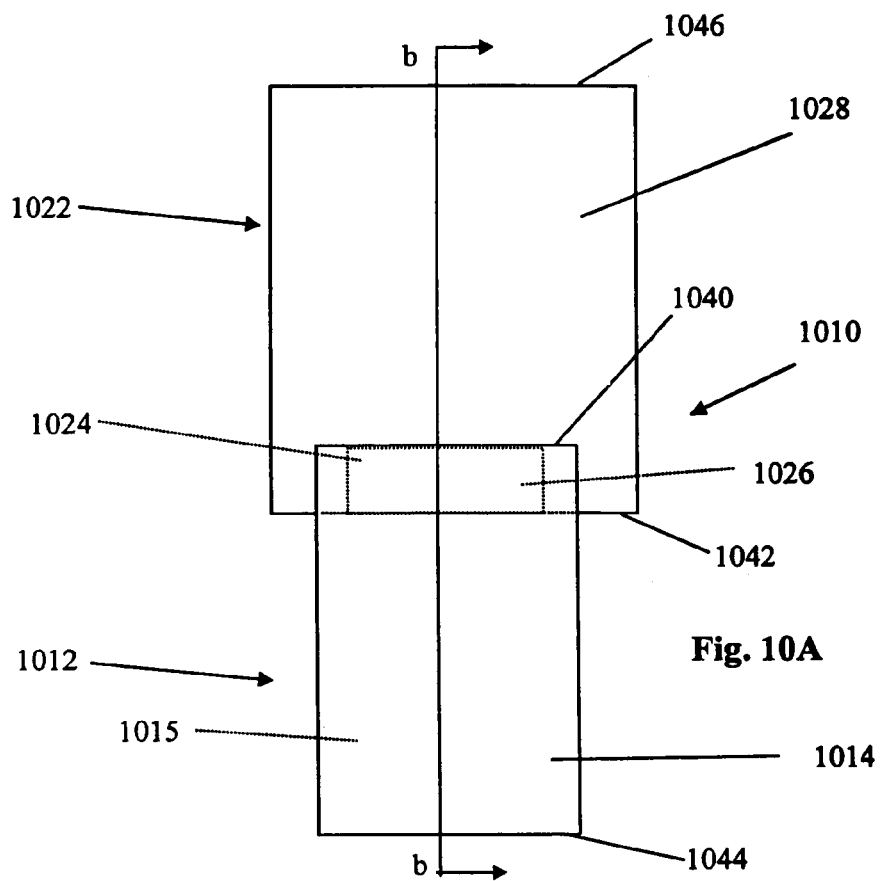
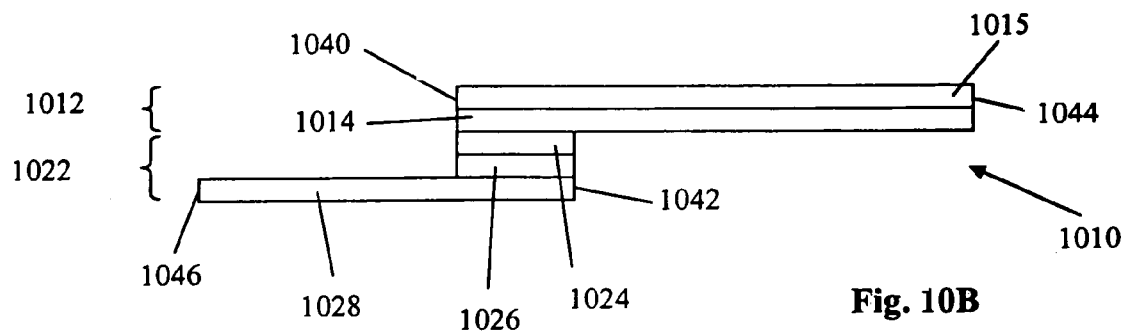
Fig. 10A
Fig. 10B

NON-TACKY ADHESIVE FASTENING SYSTEM FOR USE IN CONSUMER PRODUCTS

FIELD OF THE INVENTION

The present invention relates to a non-tacky adhesive fastening system having a non-tacky adherent and a non-tacky adherend in a pre-engaged configuration that may be peeled apart with a low force while maintaining adequate refastenability. More particularly, the present invention relates to consumer goods having such a fastening system which provides refastenability.

BACKGROUND OF THE INVENTION

Fastening systems are widely used in a variety of applications where closure of components is required. Certain fastening systems are refastenable in that they are capable of multiple openings and closures. Items such as diapers and containers storing foodstuff or other consumer goods are commonly equipped with a fastening system and, typically, a refastenable fastening system. Such fastening systems may include a mechanical fastening system and/or an adhesive fastening system. While mechanical and adhesive fastening systems provide certain consumer benefits, each system also has significant drawbacks.

Mechanical fastening systems capable of refastenability include hook and loop fasteners and variants such as mushroom-shaped fasteners. These types of mechanical fasteners may have a tendency to attach to undesired surfaces such as clothing, carpet, or the wearer. Furthermore, hooks are generally rigid and may be a source of irritation if used in products which are placed in close contact to a wearer's skin. Another problem often associated with mechanical type fasteners is that they may become damaged during the high-speed formation process required for commercially viable manufacture of consumer goods such as diapers. For example, hooks tend to get damaged during manufacture, and other mechanical type fasteners such as buttons, tab and slots, or the like can also become damaged, torn, or otherwise impacted by high speed handling.

Another problem associated with mechanical fasteners is that they may not exhibit the requisite integrity for use in consumer goods. For example, disposable absorbent articles such as pant-type diapers may have sides secured by a mechanical fastener such as a hook and loop fastening system. However, hook and loop fastening systems may prove inadequate for the peel force demands of a pant-type diaper. If peel forces are too low, a child may be able to remove the diaper when such removal is undesired. Another potential drawback of conventional mechanical fasteners, particularly in pant-type diapers, is that such fasteners may need to be located in an area of the diaper without stretch properties. This may create a design paradox if the mechanical fastener is to be located in an area exhibiting stretch properties such as the side panels of a pant-type diaper. The compromise made is typically to limit the size of the hook and loop fastening area which results in a lack of versatility of the product and can diminish the desired fastening strength of the side panels of the article.

Like mechanical fastening systems, adhesive fastening systems also have drawbacks. One such drawback of an adhesive fastening system includes the use of a traditional adhesive that sticks to surfaces indiscriminately. Such indiscriminate adhesive fastening systems are not ideal for use in consumer products such as diapers where adhesion of the fastener to skin, hair, or clothing is undesirable.

Another drawback of adhesive fastening systems is that the system may exhibit "lock-up" after a period of time in an engaged configuration. Lock-up is the condition where an engaged fastening system will not release without some form of catastrophic failure that prohibits refastening. For example, the fastening system may tear or the adhesive may delaminate from an underlying substrate. In many consumer goods with an adhesive fastening system, lock-up is a significant problem because the consumer good is manufactured with the fastening system already engaged (i.e., pre-engaged). For example, an absorbent article with a pre-engaged adhesive fastening system can take the form of a pants-type diaper having refastenable side seams comprising an adhesive fastening system. During the manufacture, transport, and storage of pant-type diapers, a pre-engaged adhesive may be engaged for several weeks or months and may experience elevated pressure and temperature.

Time, temperature, and pressure may all exacerbate adhesive lock-up. Generally, a pre-engaged adhesive fastening system will experience environmental factors during transport and storage that far exceed the environmental factors experienced during use of the pre-engaged adhesive fastening system. For example, during transport and storage, a pre-engaged adhesive fastening system on a pants-type diaper may experience temperatures in excess of 60° C. and pressures in excess of 0.8 N/cm$^2$. Conversely, during wear, a pre-engaged adhesive fastening system on a pants-type diaper generally experiences temperatures of about 98° F. (about 37° C.) and de minimis pressures. As a result of the time, temperature, and pressure experienced by the pre-engaged adhesive fastening system, a consumer may receive a pants-type diaper with a locked adhesive fastener. The diaper would be considered undesirable since unfastening the pre-engaged system would prevent further refastenability of the diaper.

Even if lock-up does not occur, the pre-engaged adhesive fastening system may require separation forces that exceed a preferred range. Consumer testing has shown that fastening systems that exhibit a peel force of greater than about 12 N/inch, as measured by a T-Peel test, are viewed as being difficult to separate. Consumers tend to prefer a fastening system exhibiting a peel force of less than 10 N/inch, as measured by the T-Peel Test.

A further drawback of pre-engaged adhesive fastening systems is that, if the system does not exhibit lock-up or require an excessive separation force, the system may exhibit poor refastenability. After a pre-engaged adhesive fastening system has been opened and refastened, the system should exhibit sufficient integrity such that it may remain engaged during use. The force to disengage the pre-fastened system should be sufficient to counteract the forces normally encountered during use of the fastening system. For purposes of pants-type diapers, the refastened adhesive fastening system should have sufficient strength to counteract normal wear forces (e.g., wearer movements) while remaining sealed. Furthermore, with regard to pants-type diapers, the fastening system should be able to be refastened at least three times while maintaining sufficient strength.

While the problems associated with mechanical and adhesive fastening systems have been presented in regard to pant-type diapers, the problems are equally applicable to similar fastening systems on other consumer and commercial products. For example, the fastening system may itself be a commercial good in the form of a rollstock of pre-engaged two-component tape such as a hook-and-loop tape with a hook-bearing sheet joined to a loop-bearing sheet. The rollstock may be used by a consumer to refastenably join two surfaces together. Other consumer products having similar problems with mechanical and adhesive fastening systems include overwraps or bags where resealability is desired. For example, fastening systems are becoming increasingly common on foodstuff bags (e.g., potato chip bags and the like) and on overwraps or bags housing consumer or commercial goods (e.g., diaper overwraps, tissue overwraps, and the like).

Accordingly, it would be desirable to provide a pre-engaged fastening system that, after aging, does not exhibit lock-up and that does not require excessive force for separation. It is also desirable that the pre-engaged fastening system is non-tacky. It is also desirable that the fastening system exhibit refastenability such that the fastening system can be opened and refastened multiple times while maintaining sufficient integrity in the refastened state. Pre-engaged adhesive fastening systems are desirable because, in a pre-engaged configuration, the adhesive surface is not exposed to contamination during shipment and handling.

It is also desirable to provide consumer goods comprising a pre-engaged fastening system that does not exhibit lock-up, does not require excessive force for separation, and exhibits requisite refastenability. A pre-engaged adhesive fastening system may impart desirable characteristics to a product that incorporates such a system. With regard to absorbent articles such as pant type-diapers, by employing various types of non-tacky adhesive fastening techniques either alone or in combination with other fastening techniques, the articles described herein offer improved versatility, fit, and refastening performance over those previously known in the art. These and other advantages of the present invention will become apparent in light of the description below.

SUMMARY OF THE INVENTION

In light of the problems with current fastening systems, the present invention relates to a non-tacky adhesive fastening system comprising an engaging member having an engaging surface with a non-tacky adherent disposed thereon and a receiving member having a receiving surface with a non-tacky adherend disposed thereon. The non-tacky adherent is pre-engaged to the non-tacky adherend. The non-tacky aged fastening system exhibits a T-Peel of less than about 12 N/inch and is refastenable.

The present invention also provides for an absorbent article comprising an absorbent assembly, a pair of side panels wherein each side panel comprises a front side panel and a rear side panel, and a non-tacky adhesive fastening system comprising a non-tacky adherent and a non-tacky adherend. The absorbent assembly comprises a liquid permeable topsheet, a backsheet, and an absorbent core disposed therebetween. The absorbent assembly has a front waist region, a rear waist region and a crotch region between and connecting said front and said rear waist regions. The non-tacky adherent and the non-tacky adherend are pre-engaged thereby joining the front side panel and the rear side panel. The pre-engaged non-tacky aged adhesive fastening system exhibits a T-Peel of less than about 12 N/inch and is refastenable. The absorbent article may have an intermediate side panel disposed between the front side panel and the rear side panel.

The present invention also relates to an absorbent article comprising an absorbent assembly, a pair of side panels, and a non-tacky adhesive fastening system comprising a non-tacky adherent and a non-tacky adherend. The absorbent assembly comprises a liquid permeable topsheet, a backsheet, and an absorbent core disposed therebetween. The absorbent assembly has a front waist region, a rear waist region, and a crotch region between and connecting said front and said rear waist regions. The non-tacky adherent and the non-tacky adherend are pre-engaged to join the side panel and the waist region. The pre-engaged non-tacky aged adhesive fastening system exhibits a T-Peel of less than about 12 N/inch and is refastenable.

The present invention also provides for a disposable absorbent article comprising a waistband having a front region and rear region; an absorbent assembly having a front waist region, a rear waist region, and a crotch region between and connecting said front and said rear waist regions; and a non-tacky adhesive fastening system. The rear waist region of the absorbent assembly is joined to the rear region of the waistband. The absorbent assembly comprises a liquid permeable topsheet, a backsheet, and an absorbent core disposed therebetween. The non-tacky adherent and non-tacky adherend are pre-engaged thereby joining the absorbent assembly front waist region to the waistband front region. The pre-engaged non-tacky aged adhesive fastening system exhibits a T-Peel force of less than about 12 N/inch and is refastenable.

The present invention also relates to an article of commerce comprising at least one commercial good and an overwrap partially or fully enclosing said commercial good. The overwrap comprises an opening through which the commercial good may be removed. The article of commerce also comprises a pre-engaged non-tacky adhesive fastening system comprising a non-tacky adherent disposed on a first area of the overwrap and a non-tacky adherend disposed on a second area of the overwrap, wherein the non-tacky adherent and non-tacky adherend are pre-engaged thereby joining the first area of the overwrap to the second area of the overwrap and sealing the opening. The pre-engaged non-tacky aged adhesive fastening system exhibits a T-Peel force of less than about 12 N/inch and is refastenable.

BRIEF DESCRIPTION OF THE DRAWINGS

FIG. 1A is a plan view of an exemplary fastening system.

FIG. 1B is a cross-sectional view of the fastening system of FIG. 1A taken along sectional line 2-2.

FIG. 10A is a plan view of a representative sample for the Shear Hang Time test.

FIG. 10B is a sectional view of the sample of FIG. 10A taken along sectional line b-b.

DETAILED DESCRIPTION OF THE INVENTION

Figure 2A:
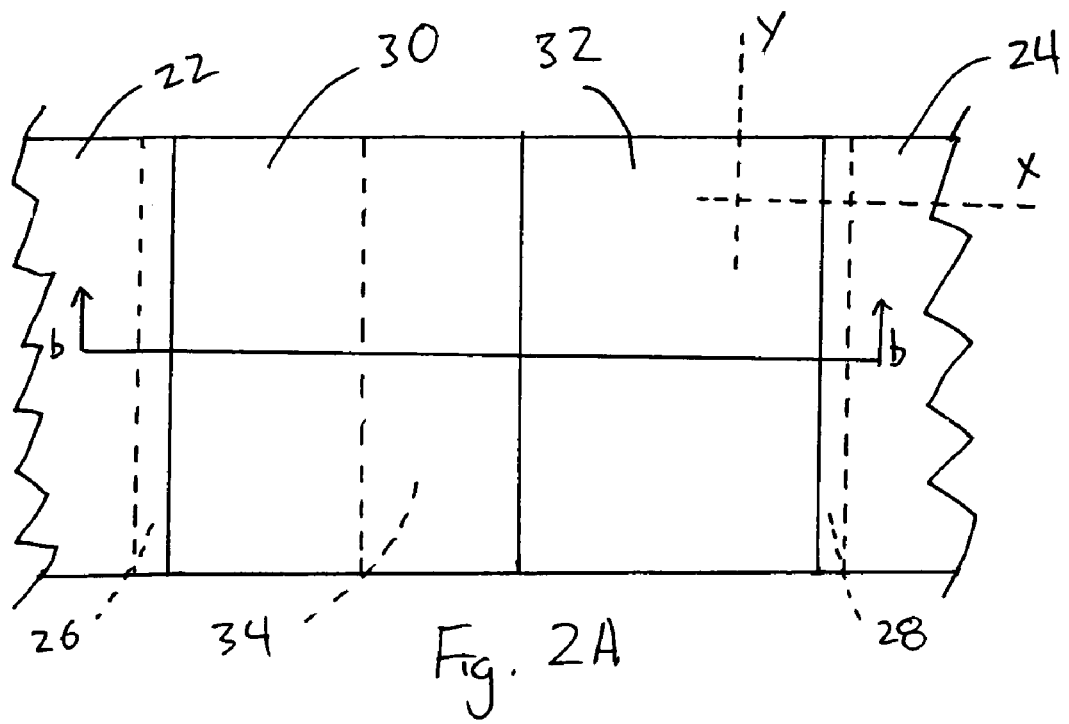
FIG. 2A is a plan view of another exemplary fastening system.

As used herein, the term "absorbent article" refers to a device that absorbs and contains liquid, and more specifically, refers to a device that is placed against or in proximity to the body of the wearer to absorb and contain the various exudates discharged from the body. Absorbent articles include items such as diapers, pull-on diapers or pant-type garments, training pants, incontinence briefs, incontinence undergarments, absorbent inserts, diaper holders and liners, feminine hygiene garments, and the like.

As used herein, the term "longitudinal" refers to a direction running perpendicular from a waist edge to an opposing waist edge of the article and generally parallel to the maximum linear dimension of the article. Directions within 45 degrees of the longitudinal direction are considered to be "longitudinal."

As used herein, the term "lateral" refers to a direction running from a side edge to an opposing side edge of the article and generally at a right angle to the longitudinal direction. Directions within 45 degrees of the lateral direction are considered to be "lateral."

As used herein, the term "disposable" is used to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the terms "elastic," "elastomer," and "elastomeric" refer to a material which generally is able to extend to a strain of at least 50% without breaking or rupturing, and is able to recover substantially to its original dimensions after the deforming force has been removed.

As used herein, the term "body-facing" is used to describe a surface that is in contact with the body of a wearer or in close proximity (i.e., closer to the body than a garment-facing surface) to the body of the wearer when the article is worn.

As used herein, the term "garment-facing" is used to describe a surface that is in contact with or may be in close proximity to any garment being worn.

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "pant-type" refers to an article configured such that it has a waist opening and a pair of leg openings. A pant may be placed in position on the wearer by inserting the wearer's legs into the leg openings and sliding the pant into position about a wearer's lower torso. This configuration may be permanent as in the case of conventional underwear, or may be temporary as in the case of a training pant with openable seams for removal. Additionally, absorbent articles can be constructed with refastenable features allowing the article to have both a pant-like configuration and one or more configurations which are open or not pant like.

As used herein the term "refastenable" refers to the attachment of two or more elements or portions of elements together in a manner in which they can be separated and re-attached without substantial degradation of fastener performance or damage to surrounding components of the article which would impair the article's continued use. It will be appreciated that a refastenable component need not have an infinite life span, but it is sufficient that the components attached in a refastenable manner can be separated and re-attached successively several times over the typical use life span of the article. It will also be appreciated that the aggressiveness of actual fastening may be reduced significantly from fastening to refastening in absolute terms, but that such reduction is not "substantial degradation" of fastener performance if the resulting refastened strength is sufficient for the fastening system's purpose of use.

As used herein, the term "refastening event" refers to the separating and reengaging of an engaged fastening system.

As used herein, "lock-up" refers to the condition where an engaged fastening system will not release without some form of catastrophic failure that prohibits refastening.

As used herein "permanent bond" refers to attachment of two or more elements or portions of elements together in a manner in which they are not intended to be separated during normal use of the article. Separation of such a permanent bond results in degradation of the attachment and/or of portions of the article. The performance of the article for its intended use is compromised upon breaking of a permanent bond.

As used herein, "adhesive fastening system" refers to a fastening system utilizing a traditional adhesive, a selective adhesive, or a cohesive for adhesion.

As used herein the term "mechanical fastener" refers to a fastening system or mechanism relying on physical restraint, magnetic fields, or engagement of portions of the fastener for operation. Examples of mechanical fasteners are hook and loops, hooks and hooks, buttons, snaps, tab and slot, zippers, magnet(s), and tongue and groove fasteners.

As used herein, the terms "typical adhesive" and "traditional adhesive" are interchangeable and refer to an adherent which demonstrates adhesion when applied to another material generally (e.g. material is not specially selected). Traditional adhesive materials connect to other materials indiscriminately and may stick to a variety of materials. Traditional adhesives are tacky. Generally, typical adhesive materials used in disposable absorbent articles demonstrate adhesion either at certain temperatures (such as a hot melt adhesive) or under pressure (a pressure sensitive adhesive).

As used herein, the term "oriented" refers to a polymer material that has been strained during manufacture to substantially align the molecular chains. "Bi-oriented" refers to a material that has been strained during manufacture in two directions; generally, the two directions are orthogonal to each other.

As used herein, the term "cohesive" refers to a material that demonstrates surface interaction (in terms of connection of one surface to another) when applied to itself or to an analog of itself (i.e., the same or essentially the same material is both the adherent and adherend). An A-A type cohesive material will fasten or form a connection primarily to itself. Generally, such cohesives are substantially non-tacky (such as to skin) at room temperature or while under moderate pressure (e.g., finger pinch pressure).

As used herein, the term "selective adhesive" refers to an adherent which demonstrates surface interaction (in terms of connection of one surface to another) when applied to a specially selected adherend. An A-A' type selective adhesive system demonstrates surface interaction where adherent A will stick to adherend A', where A' is a material that is chemically similar to A. An A-B type selective adhesive system demonstrates surface interaction properties where adherent A will stick to different material, adherend B. However, it should be noted that A' may also be a cohesive. For example, in an A-A' type selective system, A may also attach to A, and A' may attach to A'. In another example, an A-B type selective adhesive system could also exist where an material A may attach to itself or to material B, but material B will not attach to itself. The adherent and adherend of selective adhesives may be non-tacky.

As used herein the term "non-tacky" refers to an adherent or adherend that exhibits low surface adhesion to skin as measured by Probe Tack Test Method described below. Low surface adhesion is quantified as a measurement of less than 50 grams force (gf) according to the Probe Tack Test Method. In certain embodiments, low surface adhesion may be less than 40 gf; alternately, less than 30 gf; alternately, less than 20 gf; alternately, less than 10 gf; or alternately, less than 5 gf. Conversely, "tacky" refers to an adherent or adherend that exhibits a surface adhesion to skin as measured by Probe Tack Test Method described below of greater than 50 grams force (gf) as measured by Probe Tack Test Method.

As used herein the term "dwell time" refers to the time a fastening system remains engaged. Generally, the dwell time is the time a fastening system remains engaged prior to some testing of the engaged fastening system.

As used herein the term "aging" refers to the process by which a fastening system (i.e., typically a pre-engaged fastening system) remains engaged over some period of time. Aging may occur when (i) a pre-engaged fastening system is engaged for approximately 15 days after manufacture or (ii) a fastening system is initially engaged and then subjected to an accelerated aging process. Similarly, the term "aged" refers to a fastening system (i.e., typically a pre-engaged fastening system) that has been subjected to aging.

As used herein, "accelerated aging process" refers to an engaged fastening system being subjected to a temperature of 60° C. and an evenly distributed pressure of 0.8 N/cm$^2$ for at least 3 days. The accelerated aging process may be prolonged to 7 days or more; however, unless specifically designated otherwise, accelerated aging is performed for 3 days. The accelerated aging process is believed to simulate the effect of aging the engaged fastening system for several weeks after manufacture (e.g., while the product is stored, transported, etc.).

As used herein the term "extensible" refers to materials which elongate or increase in at least one dimension when subject to an external pulling force.

As used herein the terms "stretchable" or "elastic" refer to materials which are extensible and which also return to substantially their original dimensions when the external pulling force is removed. It will be appreciated that the terms stretchable and elastic include the term extensible as each term is used herein.

As used herein the term "pre-engaged" refers to a fastening system that is manufactured so that elements of the non-tacky adhesive fastening system are engaged, affixed, or otherwise stuck together.

The present invention in one aspect relates generally to a pre-engaged non-tacky aged adhesive (PENTA) fastening system that exhibits requisite refastenability. The PENTA fastening system should exhibit no lock-up and should require minimal separation force. The present invention in another aspect relates generally to a consumer good comprising a PENTA fastening system. Such a fastening system may be useful for any product that requires both (i) an initial attachment or seal and (ii) refastenability that maintains sufficient fastening integrity. Exemplary products include, but are not limited to, polymer film bags such as for diaper, wipe, or tissue containers, and disposable absorbent articles such as diapers or pull-on pants. A particular aspect of the present invention relates to a disposable absorbent article having a PENTA fastening system. The pre-engaged fastening system joins elements of the article so that the article may be provided to the consumer in a closed, "pant-like" configuration (i.e., the article has a complete waist opening and a pair of leg openings). In contrast, an article may be provided in an "open" configuration (i.e., the fastening system is not pre-engaged and the article does not have a continuous waist and/or a pair of leg openings) where the consumer must engage the fastening system to form a continuous waist and enable the article to encircle the waist and legs of a wearer. In either a closed or open form, the user may make use of the refastenability feature to (i) open the waist from a closed to open configuration or to (ii) close it from an open to closed configuration. The refastenable feature allows for such opening and closing of a portion of the article multiple times during the life cycle of the absorbent article.

FIG. 1A shows an exemplary PENTA fastening system according to the present invention. FIG. 1B shows a cross-sectional view of the exemplary PENTA fastening system of FIG. 1A taken along sectional line 2-2. The system 20 generally comprises an engaging member 22 and a receiving member 24. The engaging member 22 may have an engaging surface 26 with a non-tacky (NT) adherent 30 disposed thereon. The receiving member 24 may have a receiving surface 28 with a non-tacky (NT) adherend 32 disposed thereon. In a pre-engaged state, the engaging surface 26 of the engaging member 22 may be in a planar face-to-face relation to the receiving surface 28 of the receiving member 24. The engaging member 22 and receiving member 24 may be positioned so the NT adherent 30 and the NT adherend 32 contact at an interface 34. The NT adherent 30 and the NT adherend 32 interact so as to join the engaging member 22 and the receiving member 24. The PENTA fastening system 20 is generally planar with an x-axis and a y-axis, perpendicular to the x-axis, as shown in FIG. 1A. The PENTA fastening system 20 may have some caliper along a z-axis, shown in FIG. 1B, which is perpendicular to the plane formed by the x-axis and the y-axis. As will be appreciated in the description provided below, the PENTA fastening system 20 may experience a shear force that generally may be directed along the x-axis or along any vector in the x-axis/y-axis plane. As will be further appreciated in the description provided below, the PENTA fastening system 20 may experience a peel force that generally may be directed along the z-axis.

Figure 2B:
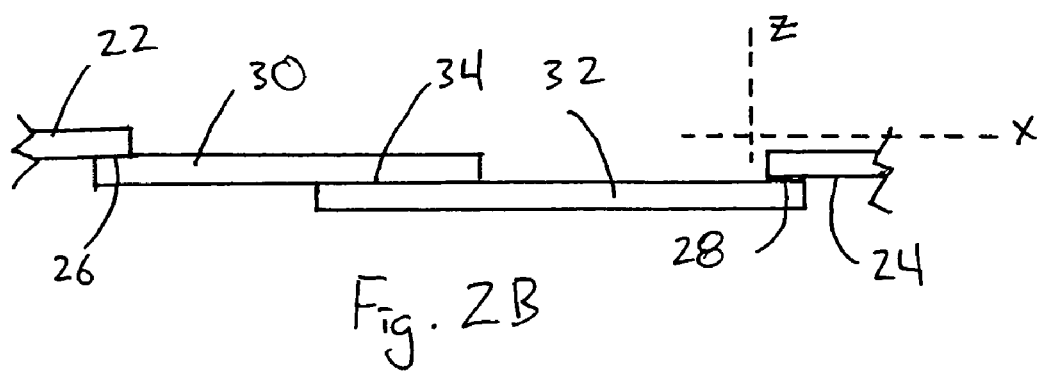
FIG. 2B is a cross-sectional view of the fastening system of FIG. 2A taken along sectional line b-b.

In other embodiments, such as exemplified by the plan view of FIG. 2A and the cross-sectional view of FIG. 2B taken along sectional line b-b, the NT adherent 30 and/or the NT adherend 32 may be partially joined to the engaging member 22 and receiving member 24, respectively. The interface 34 between the NT adherent 30 and the NT adherend 32 may be remote from, non-overlapping with, and/or non-coterminous with the engaging surface 26 or the receiving surface 28.

It is desirable that the PENTA fastening system 20 not lock-up after aging. Lock-up occurs when the NT adherent 30 and the NT adherend 32 adhere to one another with such tenacity that, upon attempted separation of the engaging member 22 from the receiving member 24, the force of separation results in destruction of the PENTA fastening system 20 before the NT adherent 30 and NT adherend 32 separate. Destruction of the PENTA fastening system 20 entails any event that prohibits refastening of the engaging member 22 to the receiving member 24 by way of an interface of the NT adherent 30 and the NT adherend 32. For example, destruction may occur if the NT adherent 30 delaminates from the engaging member 22 before the NT adherent 30 and NT adherend 32 separate. By way of further example, destruction may occur if the engaging member 22 or receiving member 24 tears before the NT adherent 30 and NT adherend 32 separate (i.e., force of separation exceeds tensile strength of the member). Furthermore, even if lock-up of the PENTA fastening system 20 does not occur, it is desirable that the force required to separate the NT adherent 30 and the NT adherend 32 is not excessive. Since the fastening system 20 will typically be operated by hand, it is desirable that requisite separation force be targeted to the forces that may be reasonably applied by hand.

Aging of the PENTA fastening system 20 may exacerbate both lock-up and the force required to separate the PENTA fastening system 20. Aging may involve prolonged time and elevated temperature and/or pressure; all of these are factors that tend to promote lock-up. The PENTA fastening system 20 may remain engaged for several days, weeks, or months before separation occurs. For example, the PENTA fastening system 20 may be engaged during manufacture. At some later point in time, such as after transport and storage, the PENTA fastening system 20 may need to be separated. Ideally, no lock-up will be experienced. A reasonable force may be required to separate the engaging member 22 by peeling it from the receiving member 24 where peel is achieved by separation of the engaging member 22 and receiving member 24 by application of a force in generally the z-direction. Generally, the PENTA fastening system 20 should be separable in generally the z-direction with application of less than about 12.0 N/inch of force. In certain embodiments, separation should occur with between about 1.0 N/inch to about 10 N/inch of force. In certain embodiments, separation should occur with between about 2.0 N/inch to about 8.0 N/inch of force. In certain embodiments, separation should occur with about 5.0 N/inch of force. All recited separation forces in generally the z-direction are measured according to the T-Peel Test as described in the Test Methods section below. While a lower limit is not necessarily required, it may be desirable to have a lower limit on separation force value. Otherwise, the PENTA fastening system 20 may experience an untimely, spontaneous separation (i.e., the PENTA fastening system 20 may unintentionally separate due to some force experienced during transport, storage, use, or handling).

In suitable embodiments capable of being subjected to an accelerated aging process, the PENTA fastening system 20 may exhibit a minimal increase in T-Peel force over a prescribed period of time. Particularly, the PENTA fastening system 20 may exhibit a T-Peel force after 1 week of aging (at 60° C. and under 0.8 N/cm$^2$ pressure) of no more than 20% greater than the T-Peel force after 3 days of aging (at 60° C. and under 0.8 N/cm$^2$ pressure). In other embodiments, the aged, PENTA fastening system 20 may exhibit a T-Peel force after 1 week of aging (at 60° C. and under 0.8 N/cm$^2$ pressure) of no more than 15%; alternately, 10%; or alternately, 5% greater than the T-Peel force after 3 days of aging (at 60° C. and under 0.8 N/cm$^2$ pressure). In certain embodiments, the T-Peel force after 1 week of aging at 60° C. and under 0.8 N/cm$^2$ pressure is substantially the same as of the T-Peel force after 3 days of aging at 60° C. and under 0.8 N/cm$^2$ pressure (i.e., the difference in T-Peel force between the T-Peel after 1 week of aging and the T-Peel force after 3 days of aging is within the experimental error of either the 1 week or 3 day values).

In another aspect of the present invention, the PENTA fastening system 20 may exhibit a degree of adhesive strength upon refastening. Particularly for use in disposable absorbent articles, it is believed that a fastening system should maintain adhesive integrity after three refastening events (i.e., a pre-engaged fastening system is separated and re-engaged three times).

It is desirable that the PENTA fastening system 20 exhibit suitable shear strength. Shear loads are generally applied along the x-axis. Two shear values may be considered: peak shear load (i.e., dynamic shear) or sustained load over time (i.e., static shear). With regard to integrity against a static, sustained load, the PENTA fastening system 20 may exhibit a Shear Hang Time of about 50 minutes or more. Alternately, the PENTA fastening system 20 may exhibit a Shear Hang Time of about 120 minutes or more or about 240 minutes or more. Clearly, it is most desirable that the PENTA fastening system 20 exhibit a perpetual Shear Hang Time. The Shear Hang Time is measured according to the Shear Hang Time Test as described in the Test Methods section below.

With regard to integrity against a dynamic load, the PENTA fastening system 20 may exhibit a Dynamic Shear of at least about 20 N/inch$^2$. In certain embodiments, the PENTA fastening system 20 may exhibit a Dynamic Shear of at least about 30 N/inch$^2$. In other suitable embodiments, the PENTA fastening system 20 may exhibit a Dynamic Shear of at least about 40 N/inch$^2$ or of at least about 60 N/inch$^2$.

Dynamic Shear is measured according to the Dynamic Shear Test as described in the Test Methods section below.

In another aspect of the present invention, the aged PENTA fastening system 20 in a refastened configuration should not exhibit lock-up nor require excessive force for subsequent separation of the PENTA fastening system 20. In certain embodiments, the aged PENTA fastening system 20 after three refastening events (i.e., three separation and engaging events after aging) should not exhibit lock-up nor require excessive force for subsequent separation of the PENTA fastening system 20. The principles underlying lock-up of the PENTA fastening system 20 and the force required to separate the PENTA fastening system 20 in its refastened configuration are substantially the same as those presented above with respect to lock-up and force of separation with regard to the PENTA fastening system 20 in its initial aged pre-engaged state. Generally, the PENTA fastening system 20 in its refastened state should be separable with application of less than about 12 N/inch of force. In certain embodiments, separation should occur with between about IN/inch to about 10 N/inch of force. In certain desirable embodiments, separation should occur with between about 2 N/inch to about 8 N/inch of force. All recited separation forces are measured according to the T-Peel Test as described in the Test Methods section below after three refastening events. Furthermore, the refastened PENTA system 20 may exhibit the shear hang time and dynamic shear values as recited above.

The PENTA fastening system 20 or a refastened PENTA fastening system may exhibit any combination of the above cited characteristics including T-Peel force, shear hang time, and/or dynamic shear force.

Generally, the engaging member 22 and the receiving member 24 may be any two items that can be joined together or that are desired to be joined together by way of the PENTA fastening system 20. The engaging member 22 and/or the receiving member 24 may be constructed from any number of suitable substrates or materials. The engaging member 22 and receiving member 24 may be a sheet material wherein the dimensions on the largest planar face exceed, often by many orders of magnitude, the caliper or thickness of the sheet. Such sheet material may be polymeric films, metallic films, nonwoven materials, woven materials, paper, cardboard, paperboard, and combinations thereof (e.g., composites and laminates). However, the engaging member 22 and/or the receiving member 24 may be constructed from any material that is commonly used in traditional adhesive or mechanical fastening systems. In certain embodiments, the engaging member 22 and/or receiving member 24 may be constructed from a material with sufficient tensile strength that it can be processed and handled at commercially feasible speeds. In certain embodiments, the engaging member 22 may be constructed from the same material as the NT adherent 30. In certain embodiments, the receiving member 24 may be constructed from the same material as the NT adherent 32.

A variety of materials are suitable for use in the present invention as the NT adherent 30 and/or as the NT adherend 32. Suitable materials include styrenic block copolymers, polyesters, polyamides, polyisoprene, natural and synthetic rubber, olefinic homopolymers, latex, and acrylonitrile copolymers. Oriented variants of the aforementioned list may also serve as suitable cohesive materials. Surface energy modified variants of the aforementioned list may also serve as suitable materials for the NT adherent 30 and/or NT adherend 32. In certain embodiments, suitable materials include styrene conjugated diene copolymers (including polystyrene-polybutadiene-polystyrene (SBS) triblock copolymers and polystyrene-polyisoprene-polystyrene (SIS) triblock copolymers), poly(ethylene terephthalate) (PET) and surface energy modified variants, oriented polyamides and surface energy modified variants, and polyolefins (including polypropylene and polyethylene) and surface energy modified variants. Surface energy modification may occur by chemical or high-energy treatments. Suitable surface high-energy modification techniques include but are not limited to corona discharge treatment, plasma treatment, UV radiation treatment, ion beam treatment, electron beam treatment, and certain laser treatments including pulsed lasers. Suitable chemical surface energy modification techniques include, but are not limited to, the use of hydrophobic surface treatments and hydrophilic surface treatments. Other suitable materials for the NT adherent 30 and/or NT adherend 32 include webs of materials which are both elastic and provide cohesive properties as described in U.S. Pat. No. 6,156,424. In certain embodiments, suitable NT adherent 30 and NT adherend 32 combinations include SBS or SIS block copolymers/PET, SBS or SIS block copolymers/oriented polyamides, SBS or SIS block copolymers/surface modified oriented polyamides, SBS or SIS block copolymers/polyolefins, SBS or SIS block copolymers/oriented polyolefins, SBS or SIS block copolymers/surface modified polyolefins, and SBS or SIS block copolymers/SBS or SIS block copolymers.

The NT adherent 30 may be affixed to the engaging surface 26 of the engaging member 22 by any bonding means known in the art including, but not limited to, pressure bonds, thermal bonds, adhesive bonds, or ultrasonic bonds. In some embodiments, the NT adherent 30 may be extruded onto the engaging member 22 or the engaging member 22 may be extruded onto the NT adherent 30. The NT adherent 30 may be in a molten or fluid state such that, upon solidification, the material 30 is physically locked into the engaging surface. In other suitable embodiments, a hot melt adhesive may be used to affix the NT adherent 30 to the engaging member 22. The NT adherend 32 may be affixed to the receiving surface 28 of the receiving member 24 by any bonding means as presented above in regard to the NT adherent 30.

The pre-engaged non-tacky aged adhesive fastening system having any of the above described characteristics may be a component of a consumer good. For example, traditional two-sided tape (e.g., a substrate with a traditional adhesive on both planar faces) is often used for a variety of purposes in residential and commercial settings. Two-sided tape may be used, for example, to attach carpet to a floor, to attach polymer film to a window opening, or to attach pictures to a wall. Two-sided tapes allow one surface of the tape to be attached to a first material (e.g., carpet) and the other surface of the tape to be attached to a second material (e.g., a floor), whereby the first and second materials are joined. However, two-sided tapes often do not provide suitable adhesion if the first and second materials are separated and refastened.

Figure 3A:
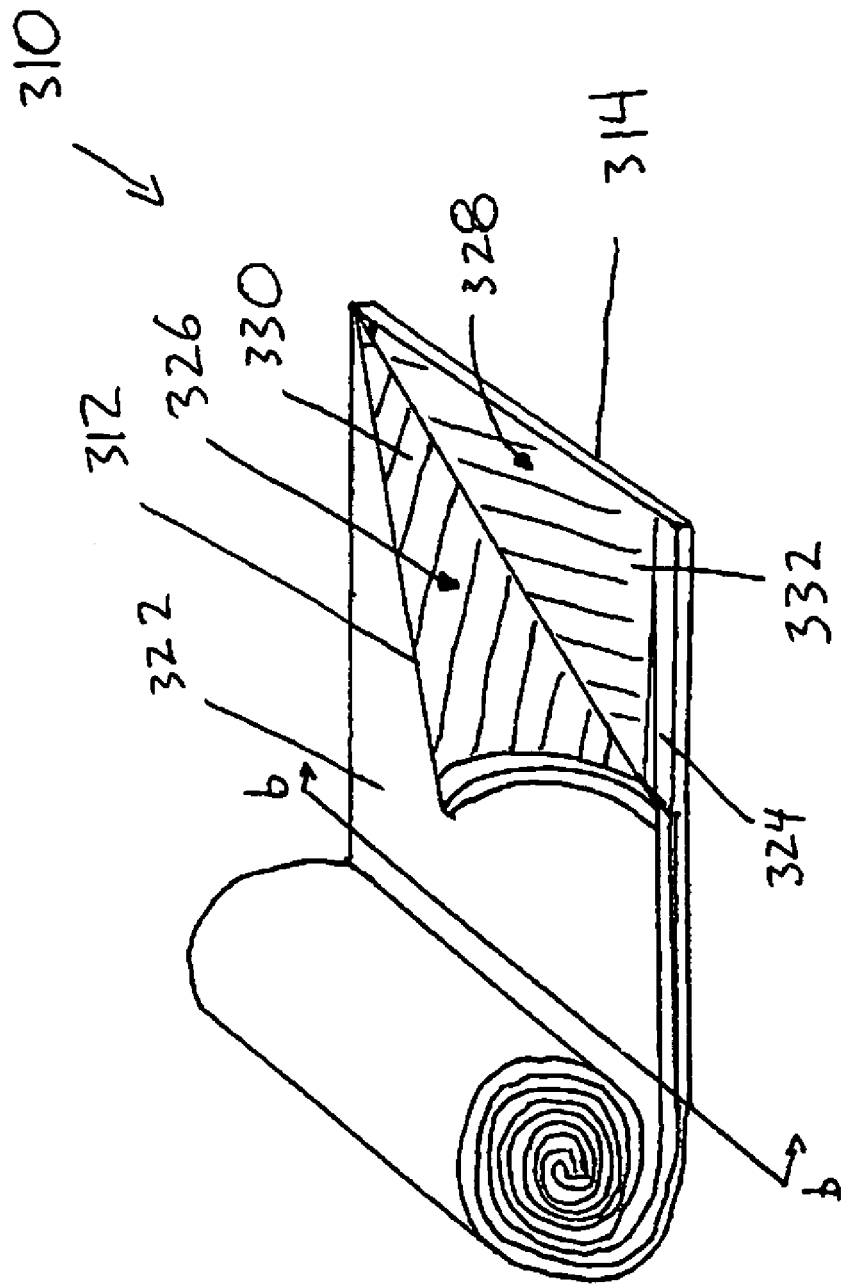
FIG. 3A is a perspective view of a rollstock of an exemplary fastening system.
Figure 3B:
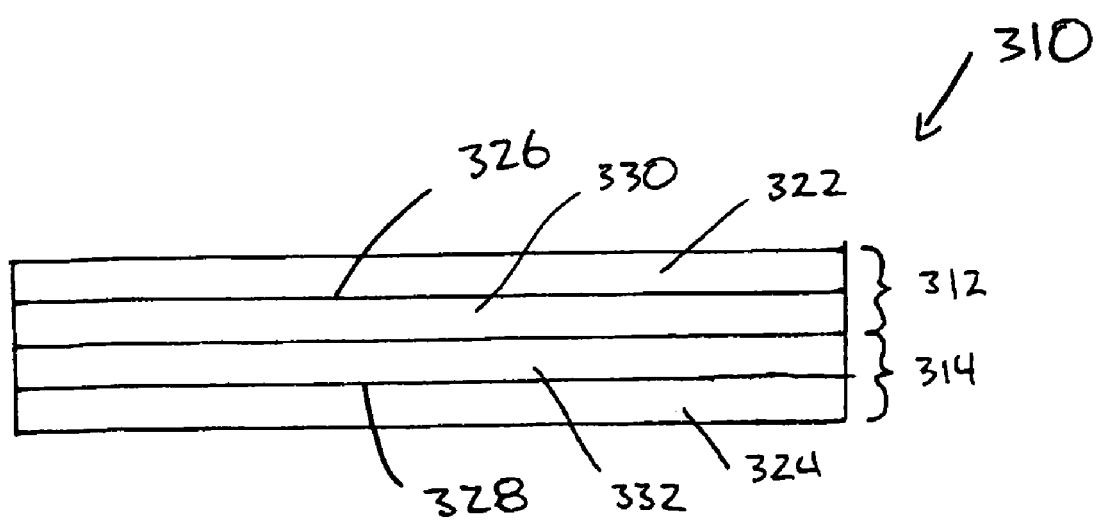
FIG. 3B is a cross-sectional view of the rollstock of FIG. 3A taken along sectional line b-b.

FIG. 3A is a perspective view of a two-component tape 310 shown as a rollstock that may be used as a replacement for two-sided tape. FIG. 3B is a cross-sectional view of the two-component tape 310 of FIG. 3A taken along sectional line b-b. The two-component tape 310 may comprise a first tape 312 and a second tape 314. The first tape 312 may include an engaging member 322 having an engaging surface 326 with a NT adherent 330 disposed thereon. The second tape 314 may include a receiving member 324 having a receiving surface 328 with a NT adherend 332 disposed thereon. The two-component tape 310 may be provided in a variety of forms such as a sheet, a ribbon, or any two dimensional shape such as a circle, square, heart, or the like. Discrete pieces of the two-component tape 310 may be packaged for transport, handling, and/or sale. A continuous piece of the two-component tape 310 may be folded, rolled, pleated, and the like for transport, handling, and/or sale. The two-component tape 310 may be used in a variety of household or commercial situations. For example, two-component tape 310 may be used in production of further consumer foods or packaging, such as the articles and overwraps described herein.

Figure 3C:
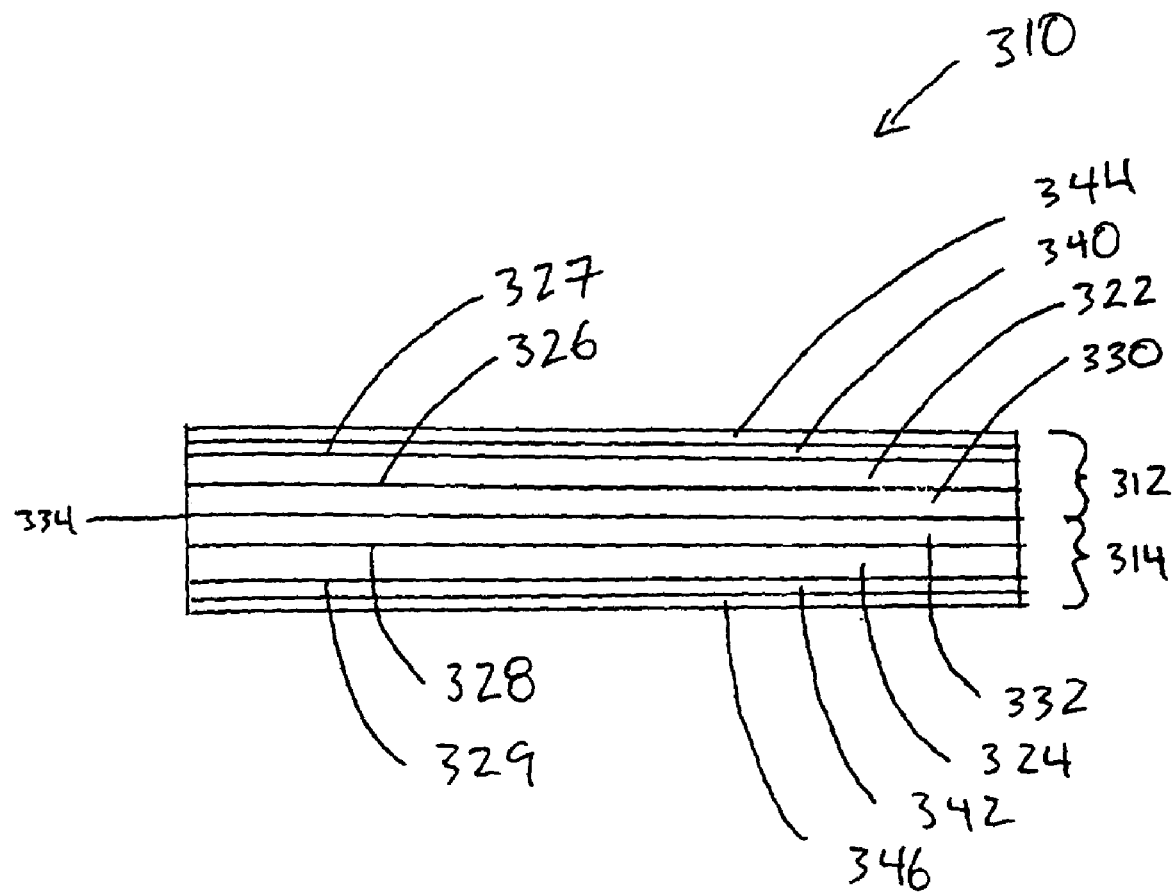
FIG. 3C is a cross-section view of an embodiment of the fastening system.

FIG. 3C is a cross-sectional view of another embodiment of the two component tape 310 comprising the PENTA fastening system and showing additional structural elements. The two-component tape 310 may comprise a first tape 312 and a second tape 314. The first tape 312 may include an engaging member 322 having an engaging surface 326 with a NT adherent 330 disposed thereon. The engaging member 322 may include a backing surface 327 opposite the engaging surface 326. An adhesive 340 may be disposed on the backing surface 327 of the engaging member 322. Release paper 344 may be placed on the adhesive 340 such that the adhesive 340 is between the engaging member 322 and the release paper 344. The release paper 344 prevents contamination of the adhesive 340 and prevents inadvertent adhesion of the adhesive 340 prior to use. The second tape 314 may include a receiving member 324 having a receiving surface 328 with a NT adherent 332 disposed thereon. The receiving member 324 may include a backing surface 329 opposite the receiving surface 328. An adhesive 342 may be disposed on the backing surface 329 of the receiving member 324. A release paper 346 may be placed on the adhesive 342 such that the adhesive 342 is between the receiving member 324 and the release paper 346. The release strip 346 prevents contamination of the adhesive 342 and prevents inadvertent adhesion of the adhesive 342 prior to use. In other embodiments, the engaging member 322 and/or the receiving member 324 may be omitted. In such embodiments, the adhesive 340, 342 may be disposed on the NT adherent 330 and NT adherend 332, respectively.

The adhesive 340, 342 may be selected from any traditional adhesive. The adhesive 340, 342 ideally will have an adhesive strength greater than that of the NT adherent 330 and the NT adherend 332. Ideally, the two-component tape should separate at an interface 334 between the NT adherent 330 and the NT adherend 332 and not at any other interface between layers of the two-component tape 310 or at the interface between the two-sided tape 310 and some other surface (e.g., carpet). Suitable adhesives 340, 342 may include traditional adhesives, selective adhesives, and/or cohesives. Traditional adhesives may allow for more varied uses of the two-component tape 310 since traditional adhesives generally exhibit adhesion to a broad spectrum of surfaces. The release paper 344, 346 may be selected based upon the particular adhesive 340, 342. The release paper 344, 346 is chosen such that it may remain affixed to the adhesive 340, 342, respectively, during handling, transport, and storage but be easily removable for end-use (e.g., such as attachment of the tape to a window frame or other surface). One suitable adhesive-release paper combination includes an adhesive available as double-sided tape code 6589 from 3M Company, St. Paul, Minn., but any similar double-sided tape may work.

A pre-engaged non-tacky aged adhesive fastening system may be a component of other consumer goods such as absorbent articles and disposable absorbent article. While a pants-type diaper is shown in FIGS. 4A-H, the non-tacky adhesive fastener may be used in other absorbent articles such as taped diapers, adult incontinence products, feminine hygiene products, and the like. The pant-type diaper 420 of FIG. 4A may include an absorbent assembly 422, side panels 460, 461, and a PENTA fastening system 440. The diaper 440 may have a front waist region 436, a back waist region 438 opposed to the front waist region 436, and a crotch region 437 located between the front waist region 436 and the back waist region 438. The periphery of the diaper 420 is defined by longitudinal edges 450 that lie generally parallel to a longitudinal centerline and the front waist edge 452 and back waist edge 454 that lie generally parallel to a lateral centerline of the diaper 20 and extend between the longitudinal edges 450.

The absorbent assembly 422 of the diaper 420 may include a liquid pervious topsheet 424, a backsheet 426, and an absorbent core 428 which may be positioned between at least a portion of the topsheet 424 and the backsheet 426. The absorbent assembly 422 may constitute the main structure of the diaper with other features added to form the composite diaper structure. The absorbent assembly 422 and generally all elements of diaper 420 may have a body-facing surface which generally is in contact with the body or in close proximity to the body when the article is worn. The absorbent assembly 422 may have a garment-facing surface opposed to the body-facing surface and which generally contacts with or may be in close proximity to any garment being worn. The topsheet 424, the backsheet 426, and the absorbent core 428 may be assembled in a variety of configurations well known in the art. Exemplary absorbent assembly structures are described in U.S. Pat. Nos. 5,899,895 and 6,120,487.

The backsheet 426 is generally that portion of the diaper 420 which is disposed adjacent the garment-facing surface of the absorbent core 428 and which prevents the excreta and/or exudates contained therein from soiling garments or other articles which may contact the diaper 420, such as bedsheets and clothing. In preferred embodiments, the backsheet 426 may be substantially impervious to liquid and may comprise any suitable thin plastic film known in the art, including a breathable film. Exemplars of suitable backsheet films include those manufactured by Tredegar Industries, Inc., Terre Haute, Ind., USA, and sold under the trade names X15306, X10962, and X10964.

The backsheet 426 may be joined to the topsheet 424, the absorbent core 428 or any other element of the diaper 420 or absorbent assembly 422 by any attachment means known in the art. For example, the attachment means may include a uniform continuous layer of adhesive, a patterned layer of adhesive, or an array of separate lines, spirals, or spots of adhesive. Exemplars of suitable adhesives include those manufactured by H.B. Fuller Company of St. Paul, Minn., USA and marketed as HL-1620 and HL-1358-XZP. Alternately, the attachment means may comprise heat bonds, pressure bonds, ultrasonic bonds, dynamic mechanical bonds, or any other suitable attachment means or combinations of attachment means known in the art.

The topsheet 424 is preferably disposed adjacent the body-facing surface of the absorbent core 428 and may be joined to the absorbent core 428 and/or to the backsheet 426 by any attachment means known in the art. The topsheet 424 is preferably compliant, soft-feeling, and non-irritating to the wearer's skin. Preferably, at least a portion of the topsheet 424 is liquid pervious, permitting liquids to readily penetrate through its thickness. A suitable topsheet may be manufactured from a wide range of materials known in the art, such as porous foams, reticulated foams, apertured plastic films, or woven or nonwoven materials of natural fibers such as wood or cotton fibers, or synthetic fibers such as polyester or polypropylene fibers, or a combination of natural and synthetic fibers. If the topsheet 424 includes fibers, the fibers may be spunbond, carded, wet-laid, meltblown, hydroentangled, or otherwise processed as is known in the art. One suitable topsheet material is a thermobonded carded web which is available as Supplier Code No. P-8 from Fiberweb North America, Inc., Simpsonville, S.C., U.S.A.

The absorbent core 428 may comprise any absorbent material which is generally compressible, conformable, non-irritating to the wearer's skin, and capable of absorbing and retaining liquids such as urine and other bodily exudates. The absorbent core 428 may be manufactured in a wide variety of sizes and shapes, for example, rectangular, hourglass, "T"-shaped, asymmetric, etc. The absorbent core 428 may include any of a wide variety of liquid-absorbent materials commonly used in disposable diapers and other absorbent articles, such as comminuted wood pulp, which is generally referred to as airfelt, cellulose wadding, meltblown polymers, chemically stiffened, modified, or cross-linked cellulosic fibers, tissue, absorbent foams including those prepared from polymerization of a high internal phase emulsion, superabsorbent polymers, absorbent gelling materials, or any other known absorbent material or combinations of materials. Exemplary absorbent core structures are described in U.S. Pat. Nos. 4,610,678 and 5,260,345.

The diaper 420 may include a variety of other structures. The diaper 420 may include at least one leg cuff. Leg cuffs are known variously in the art as gasketing cuffs, containment flaps, "stand-up" elasticized flaps, barrier cuffs, leg bands, side flaps, and/or elastic cuffs. As shown in FIGS. 4A-D, the diaper includes a pair of gasketing leg cuffs 470 and a pair of barrier leg cuffs 472. Leg cuffs 470, 472 may be constructed in any suitable configuration known in the art, including those described in U.S. Pat. No. 4,695,278 issued Sep. 22, 1987, and U.S. Pat. No. 4,795,454 issued Jan. 3, 1989.

The diaper 420 may also include a waist feature 474. The waist feature 474 may be disposed along the front waist edge 452 and/or the back waist edge 454 of the diaper 420; generally the waist feature 474 will form a portion of the front waist edge 452 and/or the back waist edge 454. The waist feature 474 may be at least laterally elastically extensible to provide circumferential tension at the diaper waist opening 462. The waist feature 474 may be constructed in any of several different configurations known in the art. Exemplary waist feature constructions include those described in U.S. Pat. No. 4,515,595 issued May 7, 1985 and U.S. Pat. No. 5,221,274 issued Jun. 22, 1993. The diaper 420 may also include side panels 460, 461 disposed in the front waist region 436 and the back waist region 438, respectively.

The diaper 420 may have a pair of front side panels 460 disposed generally transversely outward from the longitudinal edges of the absorbent assembly and at or near the front waist region 436. Similarly, the diaper 420 may have a pair of rear side panels 461 disposed generally transversely outward from the longitudinal edges of the absorbent assembly and at or near the rear waist region 438. The respective waist regions 436, 438 together with the side panels 460,461 may form a continuous waist opening 462 and leg openings 464 when the side panels 460, 461 are joined by the PENTA fastening system 440.

The side panels 460, 461 may be constructed in any suitable configuration known in the art. The side panels 460, 461 may be elastically extensible. The side panels 460, 461 may be made extensible or elastic by any of a variety of techniques known in the art. For example, an elastic side panel 460, 461 can be made by disposing an elastic member, such as elastic strands or films, between facing layers of cover material, such as a non-woven material. A suitable elastic side panel is described in U.S. Pat. No. 5,669,897. The side panels 460, 461 may be integral with the absorbent assembly 422 (i.e., they may be continuous extensions of one or more of the layers of the absorbent assembly 422) or they may be separately attached to the absorbent assembly 422. Alternately, the side panels 460, 461 may be made of multiple components or layers some of which are discrete (i.e., either attached separately to the absorbent portion or separated therefrom by a gap) and some of which are continuous. An example of this type of construction is a diaper provided with an outer nonwoven cover which completely covers all areas of the diaper 420 including the side panels 460, 461 and the absorbent assembly 422.

Figure 4A:
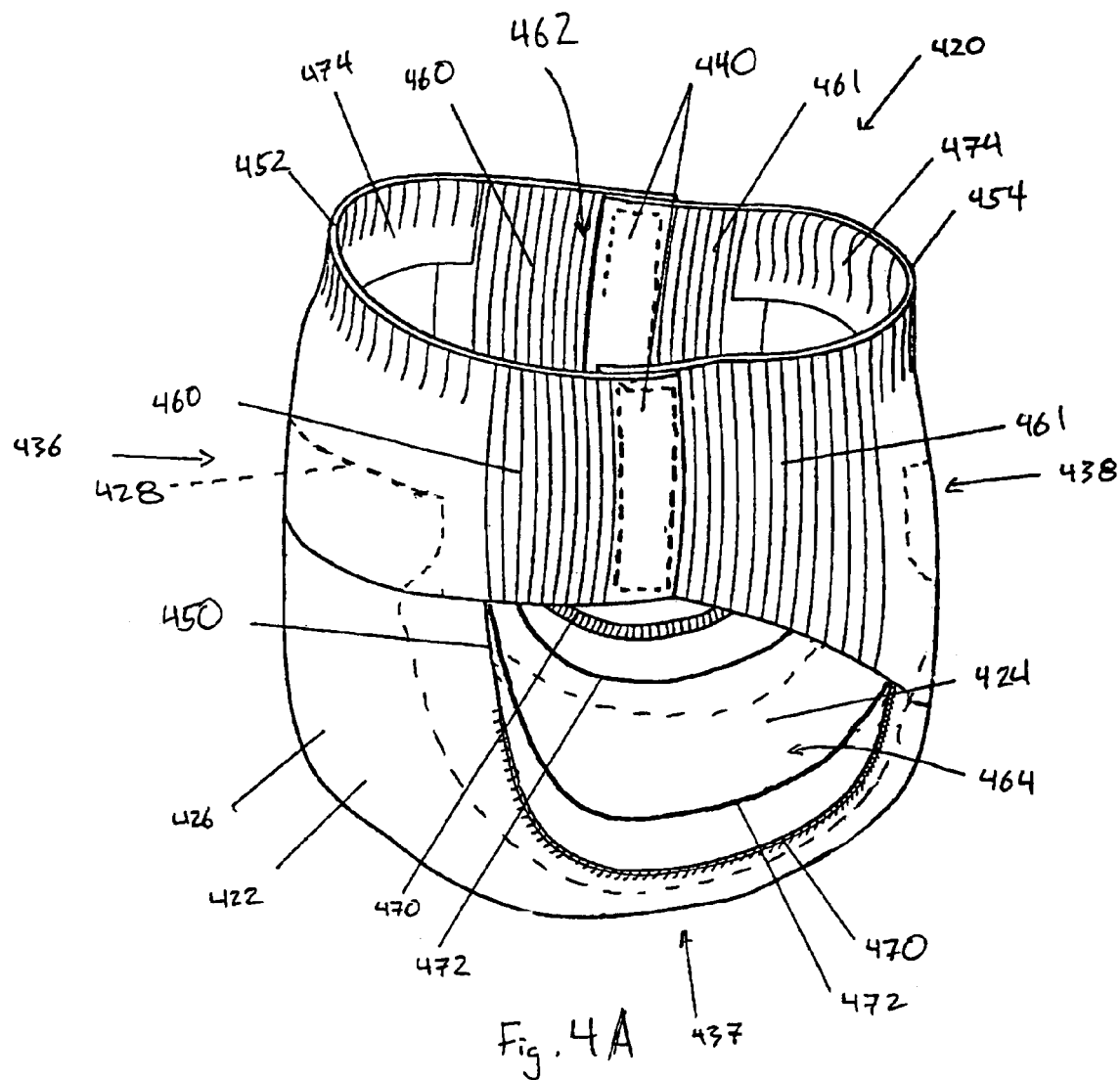
FIG. 4A is a perspective view of an absorbent article with the fastening system.
Figure 4B:
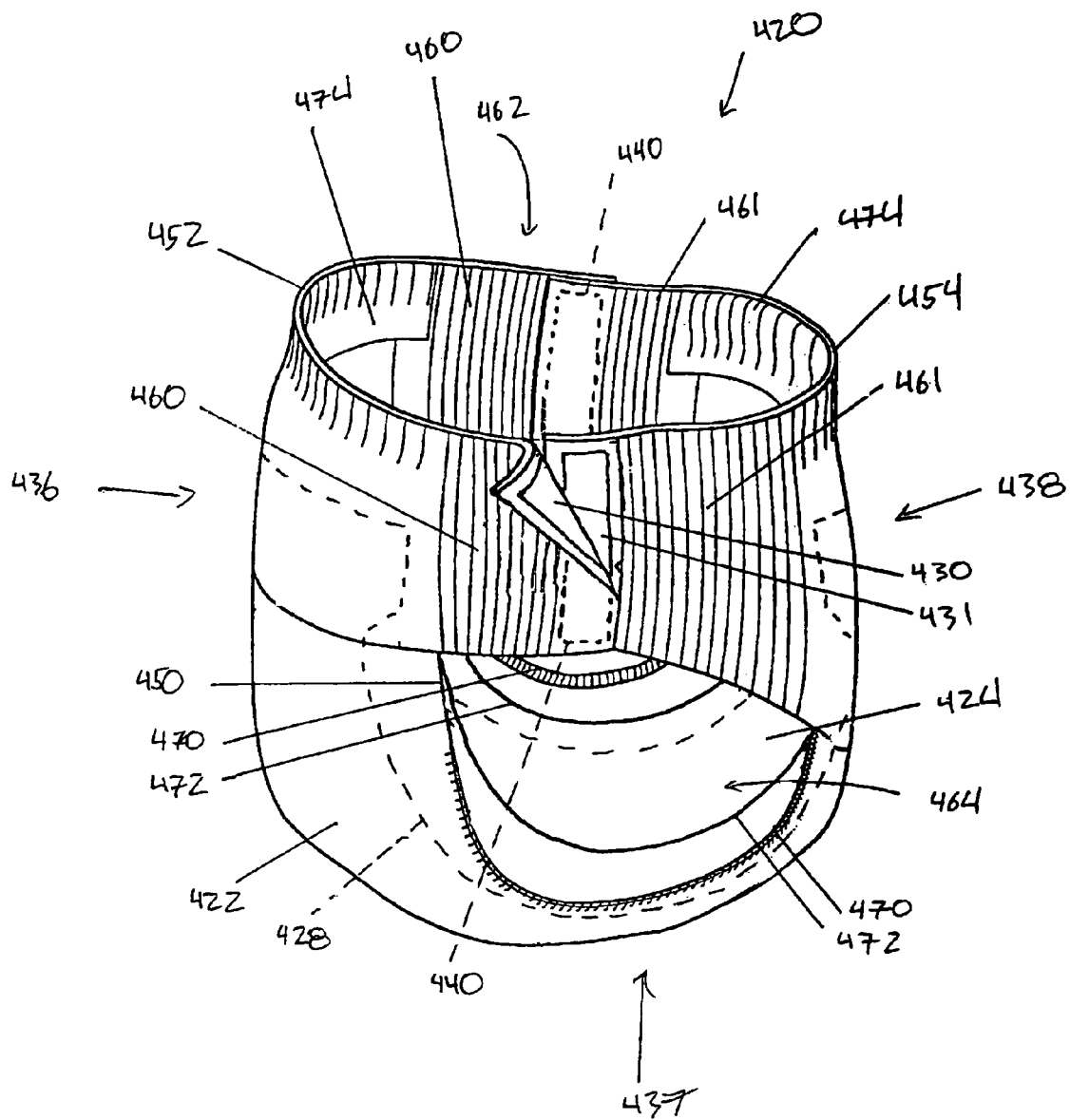
FIG. 4B is a perspective view of the absorbent article of FIG. 4A with the fastening system partially separated.

The diaper 420 may include a PENTA fastening system 440. The PENTA fastening system 440 preferably maintains the front waist region 436 and the back waist region 438 in a continuous encircling configuration during wear. As shown in FIG. 4A-B, the PENTA fastening system 440 may be disposed in proximity to the distal edge of the side panels 460, 461 where the side panels 460, 461 overlap, meet, or abut. The PENTA fastening system 440 may comprise a NT adherent 430 disposed on the front side panel 460. The NT adherent 430 is shown in FIG. 4B as being disposed on the body-facing surface of the front side panel 460. The PENTA fastening system 440 may comprise a NT adherend 431 disposed on the rear side panel 461. The NT adherend 431 is shown in FIG. 4B as being disposed on the garment-facing surface of the rear side panel 461. As should be appreciated, the NT adherent 430 and the NT adherend 431 may be disposed on any combination of the body-facing surface and/or the garment-facing surface of the front side panels 460 and/or the body-facing surface and/or the garment-facing surface of the rear side panels 461. During manufacture of the diaper 420, the NT adherent 430 and the NT adherend 431 may be joined so as to form a closed, pant-type diaper where the waist opening 462 and leg openings 464 are formed. FIG. 4B shows the diaper 420 of FIG. 4A with the PENTA fastening system 440 partially separated.

In one aspect of the present invention, the PENTA fastening system 440 may exhibit sufficient adhesive strength to maintain the diaper 420 in a closed configuration during transport, storage, and wear. The fastening system 420 may exhibit refastenability. In certain embodiments, the PENTA fastening system 440 may be separated and re-attached at least three times. Refastening of the diaper 420 is common during the application, wear, and removal. For example, the PENTA fastening system 440 provides flexibility of application. The caregiver can apply the diaper 420 in the closed, pants-type form (with the aged PENTA fastening system 440 left intact and unseparated) where the wearer steps into the diaper 420. Alternately, the caregiver can apply the diaper 420 in an open form by first separating the aged PENTA fastening system 440, applying the diaper 420 to the child (e.g., child is often lying supine), and refastening the PENTA fastening system 440. The PENTA fastening system 440 can be fastened before the diaper 420 is pulled up the wearer's legs or can be fastened after the diaper 420 is positioned ready for use on the wearer. In some cases, after application of the diaper 420 (i.e., wearer steps into the leg opening and pulls the diaper 420 up and over his or her hips), the PENTA fastening system 420 may be separated and re-attached to provide a more customized fit. During wear, the PENTA fastening system 420 may be separated to allow inspection of soiling of the diaper 420. If the diaper 420 has not been soiled, the PENTA fastening system 440 may be re-attached and diaper 420 may continue to be worn.

The NT adherent 430 and the NT adherend 431 may be disposed on the side panels 460, 461, respectively, in a variety of methods well known in the art. The NT adherent 430 and/or the NT adherend 431 may be pre-formed as a discrete element that is joined to the diaper 420 by a bonding method such as, for example, adhesive, pressure, or heat bonds. The NT adherent 430 and the NT adherend 431 may be formed on the diaper 420 during the manufacturing process of the diaper 420. For example, the NT adherent 430 and/or the NT adherend 431 may be deposited onto the diaper 420 by hot melt application, extrusion, printing, or other like methods. In certain embodiments, the NT adherent 430 and/or the NT adherend 431 may be applied in a molten form by a conventional slot coater. The NT adherent 430 and the NT adherend 431 may be disposed on the diaper 420 by the same or different methods.

Figure 4C:
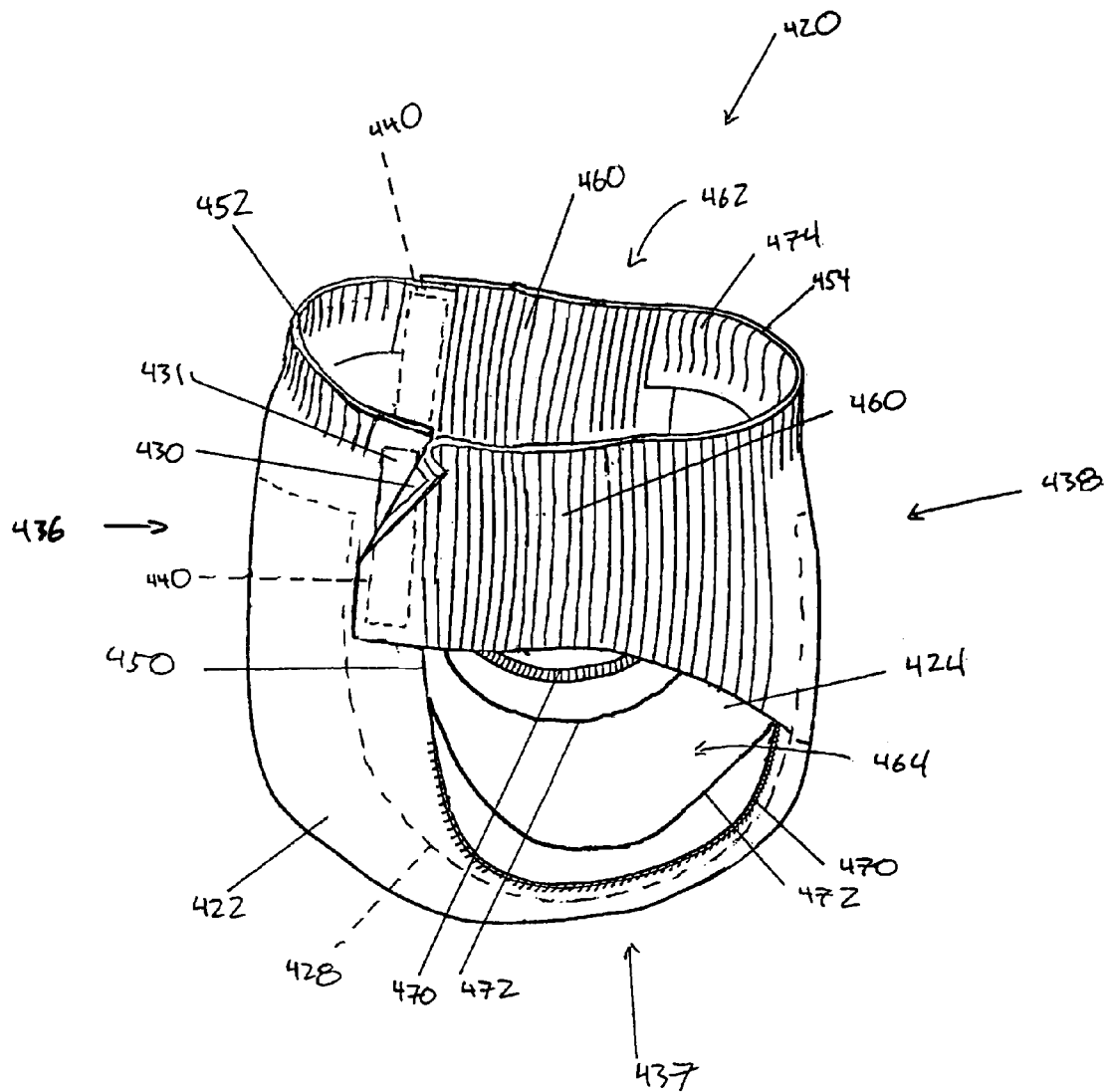
FIG. 4C is a perspective view of another embodiment of an absorbent article with the fastening system partially separated.

FIGS. 4A-B show the PENTA fastening system 440 positioned at approximately the midpoint between the front waist region 436 and back waist region 438 along the side panels 460, 461. However, in other embodiments, the PENTA fastening system 440 may be located anywhere on the diaper 420 so that the diaper 420 is presented in a closed state (i.e., continuous waist opening and leg opening formed during manufacture). FIG. 4C illustrates one embodiment of the diaper 420 where a single side panel 460 may extend between and interconnect the front waist region 436 to the rear waist region 438. The side panel 460 may be joined to and extend laterally from the longitudinal edge 450 of the rear waist region 438 of the absorbent assembly 422. The NT adherent 430 may be disposed on the body-facing surface (as shown in FIG. 4C) or the garment-facing surface of the side panel 460. The NT adherend 431 may be disposed on the garment-facing surface (as shown in FIG. 4C) or the body-facing surface of the absorbent assembly 422. The NT adherent 430 and the NT adherend 431 may generally be positioned so that the side panel 460 may overlap and attach to the absorbent assembly 422. As should be appreciated, the NT adherent 430 and the NT adherend 431 may be disposed on the absorbent assembly 422 and the side panel 460, respectively. In other embodiments, the side panel 460 may be designed to extend from the front waist region 436 so that the PENTA fastening system 440 is located in rear waist region 438 of the diaper 420.

Figure 4D:
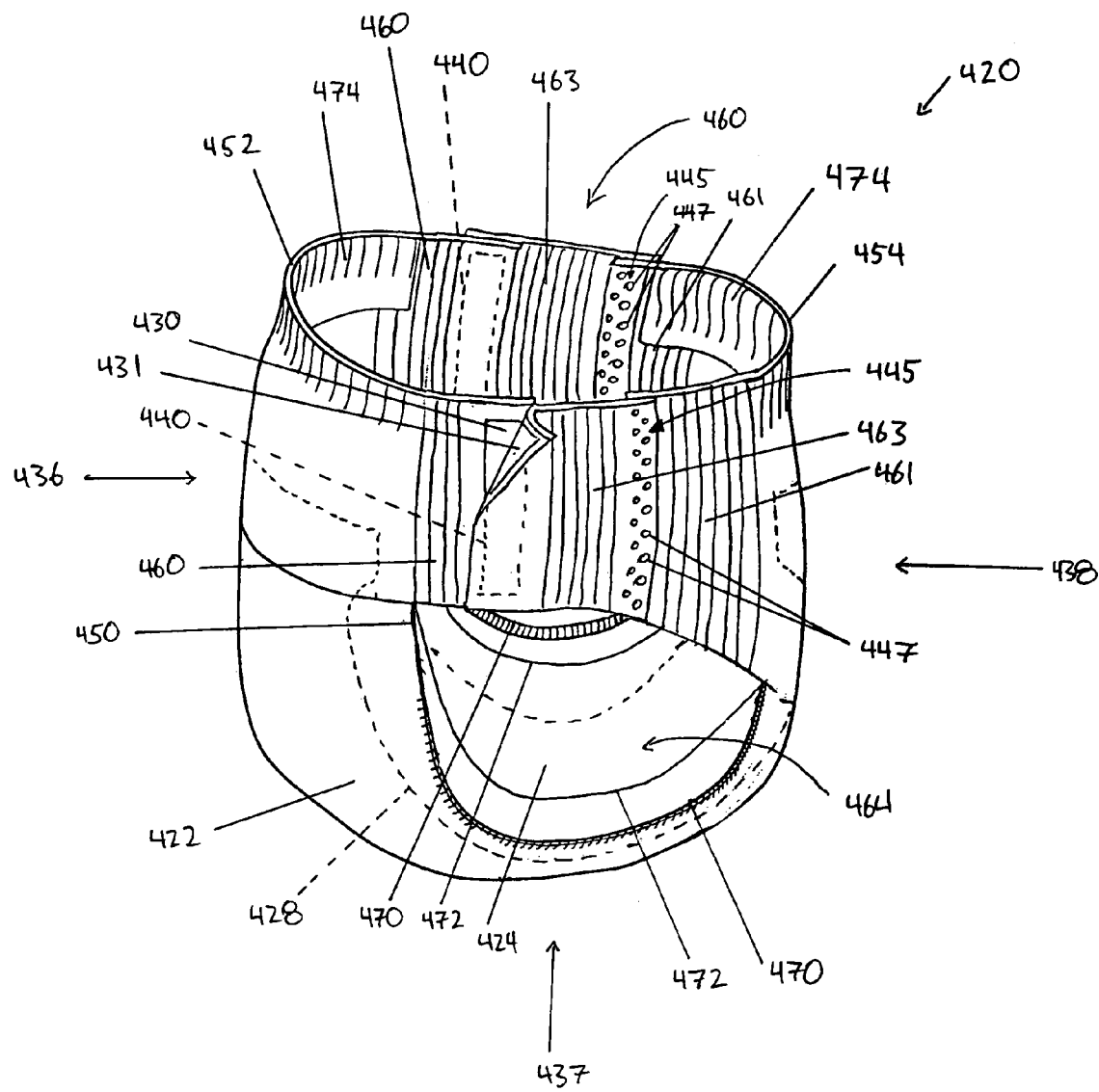
FIG. 4D is a perspective view of another embodiment of an absorbent article with the fastening system partially separated.

In another embodiment of the present invention, diaper 420 may comprise the PENTA fastening system 440 and a permanent bond 445. In a particular execution, as shown in FIG. 4D, the diaper 420 may have a pair of front side panels 460 disposed generally transversely outward from the opposing longitudinal edges 450 of the absorbent assembly 422 at or near the front waist region 436. The diaper 420 may have a pair of rear side panels 461 disposed generally transversely outward from the opposing longitudinal edges 450 of the absorbent assembly 422 and at or near the rear waist region 438. The diaper 420 may have a pair of intermediate side panels 463 each joined to or disposed between the front side panel 460 and the rear waist panel 461. The intermediate side panel 463 may be elastic, inelastic, or extensible. The front side panel 460 and the intermediate side panel 463 may be joined by the PENTA fastening system 440. The NT adherent 430 is shown as being disposed on the garment-facing surface of the front side panel 460 and the NT adherend 431 is shown as being disposed on the body-facing surface of the intermediate side panel 463. As should be appreciated, the NT adherent 430 and NT adherend 431 alternately may be disposed on the intermediate side panel 463 and front side panel 460, respectively. Furthermore, the NT adherent and NT adherend 430, 431 may be disposed on the body-facing surface and/or the garment-facing surface of the side panels 460, 463.

The intermediate side panel 463 may be permanently bonded to the rear side panel 461 by a permanent bond 445. The permanent bond 445 may be created by a variety of conventional bonding techniques including pressure, thermal, adhesive, or ultrasonic bonding. The permanent bond 445 is shown as comprising a plurality of pressure bonds 447.

During manufacture of the diaper 420 of FIG. 4D, the NT adherent 430 and the NT adherend 431 may be joined. It is believed that the use of a front, intermediate, and rear side panel 460, 463, 461 having a PENTA fastening system 440 and a permanent bond 445 may be integrated in a high speed manufacturing line more easily that a single or double panel side panel. As should be appreciated, a PENTA fastening system 440 may join both the front side panel 460 to the intermediate side panel 463 and/or the rear side panel 461 to the intermediate side panel 463. Furthermore, the PENTA fastening system 440 may join the rear side panel 461 to the intermediate side panel 463 and the front side panel 460 and the intermediate side panel 463 may be joined by the permanent bonds 445.

In other suitable embodiments, the diaper 420 may further comprise a secondary fastening system. The secondary fastening system may be a PENTA fastening system, a mechanical fastening system, or a traditional adhesive fastening system. Suitable secondary fastening systems include, but are not limited to, tape tabs, hook and loop fastening components, hook and hook fastening components, interlocking fasteners such as tabs & slots, buckles, buttons, snaps, and/or hermaphroditic fastening components, and any other known fastening means. Some exemplary surface fastening systems are disclosed in U.S. Pat. Nos. 3,848,594; 4,662,875; 4,846,815; 4,894,060; 4,946,527; 5,151,092; 5,221,274; and 6,432,098. Secondary fastening systems may comprise a first member such as an adhesive tape, a hook bearing tape, or a male fastening member (e.g., tab, button, etc.) and a second member such as a landing zone for receipt of the adhesive tape, a loop bearing surface, a hook bearing surface, or a female fastening member (e.g., a slot, button hole, etc.). As shown in FIGS. 4E-H, diaper 420 comprises the PENTA fastening system 440 as discussed above and a secondary fastening system in the form of a tab and slot fastening system 483 as disclosed in U.S. Pat. No. 6,432,098.

The tab and slot fastening system 483 may comprise a tab member 485 joined to the front side panel 460 and a slot member 487, which may have a slot 489 there through, joined to the rear side panel 461. However, the tab member 485 and the slot member 487 may be joined to the diaper 420 in other locations wherein, upon fastening of the tab member 485 and the slot member 487, the diaper 420 is placed in a closed, "pant-like" configuration (i.e. the diaper 420 has a complete waist encircling opening).

In general terms, the tab and slot fastening system 483 may be fastened by passing the tab member 485 through the slot 489 of the slot member 487. Once the tab member 485 has been passed through the slot member 487, the tab member 485 may be rotated into a plane generally parallel with the plane of the slot member 487 such that at least a portion of the tab member 485 overlaps at least a part of the slot member 487 thereby preventing the tab member 485 from slipping back through the slot 489 and disengaging the tab and slot fastening system 483. The tab member 485 and the slot member 487 may be sized to achieve this mechanical interconnection.

The tab member 485 and slot member 487 may include any material suitable for use in diaper 420, including but not limited to plastics, films, foams, nonwoven webs, woven webs, paper, laminates, steel, fiber reinforced plastics and the like, or combinations thereof. In embodiments where the fastening device is used near or against the skin of a human or animal, it may be desirable that the materials making up the tab member 485 and the slot member 487 may be flexible. However, the tab member 485 should exhibit sufficient structural rigidity so that it can not be easily pulled back through the slot 489 of the slot member 487 once fastened. The flexibility allows the tab and slot fastening system 483 to conform to the shape of the body and may reduce the likelihood that the tab and slot fastening system 483 will irritate or injure a wearer's skin. The tab member 485 and the slot member 487 may be a discrete element joined to the diaper 420 by any conventional bonding means such as pressure, thermal, adhesive, or ultrasonic bonding. The tab member 485 and the slot member 487 may be a region of an existing diaper 420 element that is rendered suitable for use as a tab member 485 or a slot member 487.

Figure 4E:
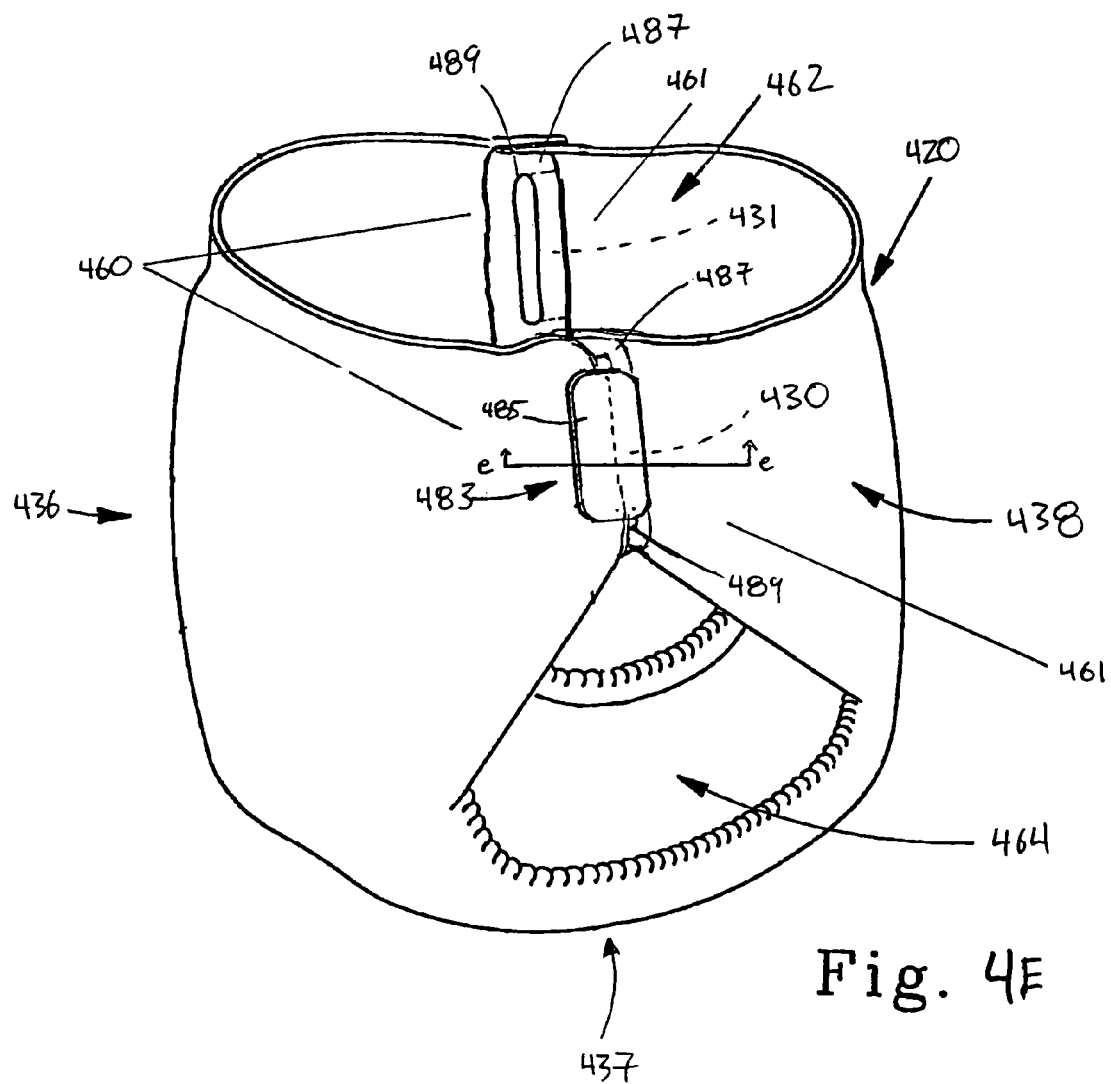
FIG. 4E is a perspective view of another absorbent article with the fastening system of the present invention and a mechanical fastening system.
Figure 4F:
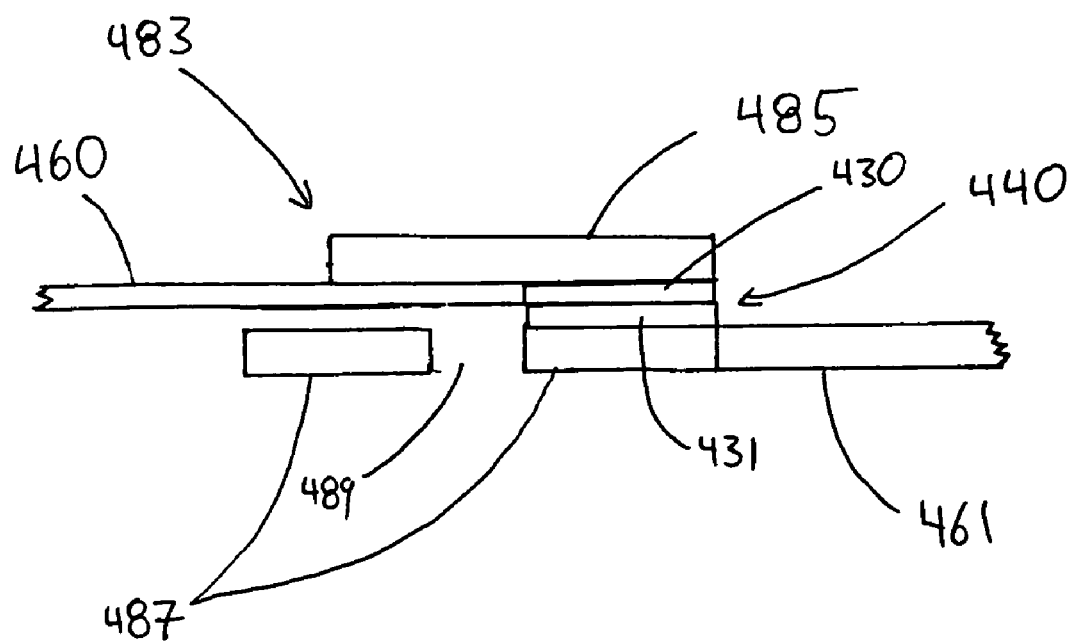
FIG. 4F is a cross-sectional view of the absorbent article of FIG. 4E taken along sectional line e-e.

In one embodiment, as shown in FIG. 4E-F, a NT adherent 430 may be disposed on at least one surface of the tab member 485. A NT adherend 431 may be disposed on at least a one surface of the slot member 487. During manufacture of the diaper 420, the tab member 485 and slot member 487 may be joined in face-to-face relationship by joining the NT adherent 430 to NT adherend 431 to form a closed, pant-like diaper. FIG. 4F is a cross-section of the tab and slot fastening system 483 and the PENTA fastening system 440 taken along sectional line e-e as shown in FIG. 4E. While not wishing to be bound by theory, it is believed that joining the tab member 485 and slot member 487 in face-to-face relationship may be simpler than inserting the tab member 485 through the slot member 487. This is believed to be particularly true when considering the line speed at which diapers are manufactured.

Figure 4G:
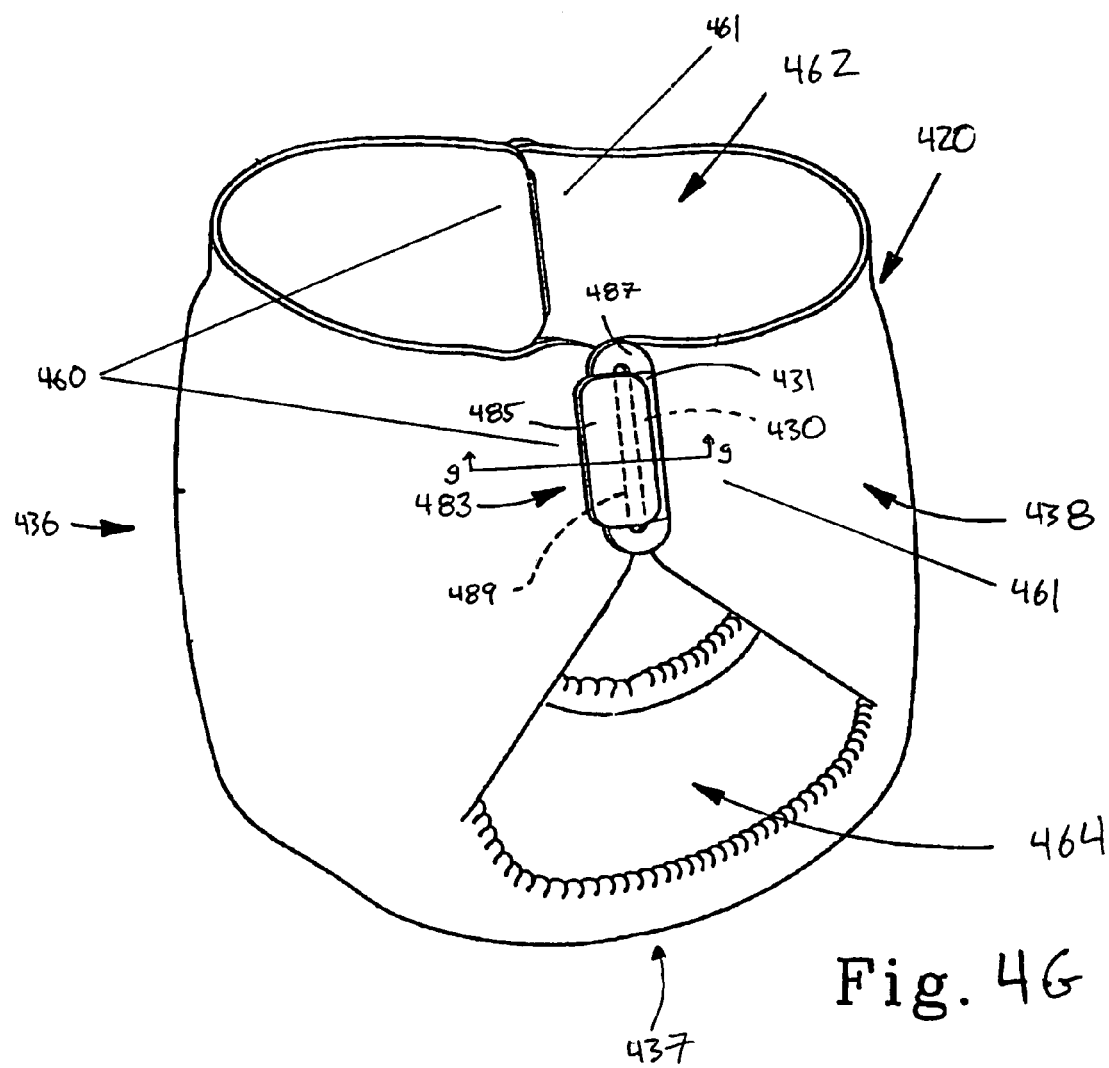
FIG. 4G is a perspective view of the absorbent article of FIG. 4E with the mechanical fastening system engaged.
Figure 4H:
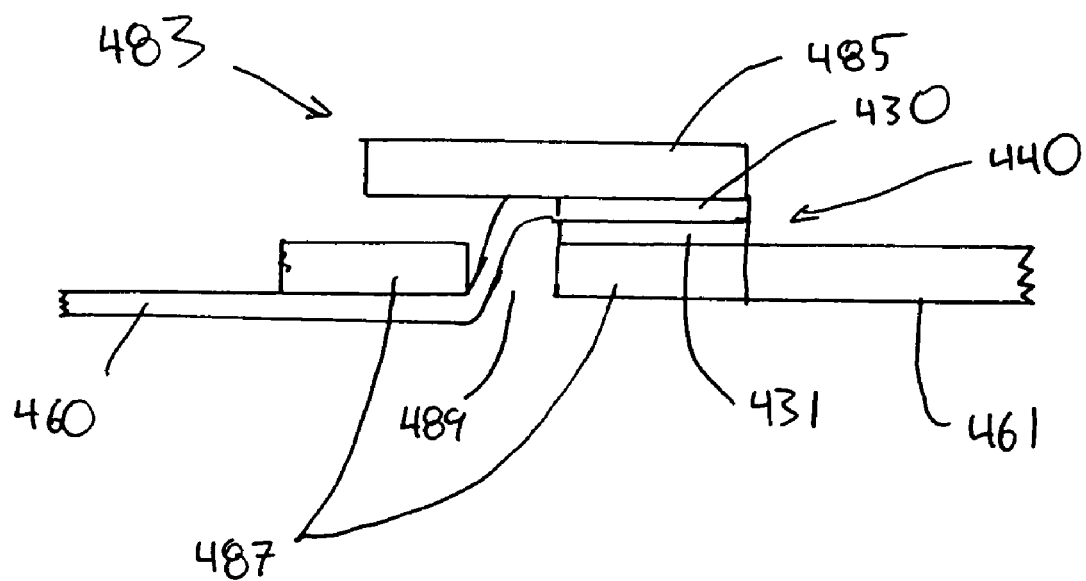
FIG. 4H is a cross-sectional view of the absorbent article of FIG. 4G taken along sectional line g-g.

The diaper 420 with a tab and slot fastening system 483 and a PENTA fastening system 440 may provide a consumer with several application options. For example, the consumer could leave the PENTA fastening system 440 engaged and pull the diaper 420 onto a wearer like a pair of pants. Once on, the consumer could leave the PENTA fastening system 440 engaged or could separate the PENTA fastening system 440 and fasten the diaper 420 by engaging the tab member 485 and the slot member 487. FIGS. 4G-H show the diaper 420 with the tab and slot fastening system 483 engaged. FIG. 4H is a cross-section of the tab and slot fastening system 483 and the PENTA fastening system 440 taken along sectional line g-g, as shown in FIG. 4G. Alternately, the consumer could separate the PENTA fastening system 440 and could apply the diaper 420 in an open-form onto the wearer. The consumer could fasten the diaper by using either the PENTA fastening system 440 or the tab and slot fastening system 483. Regardless of how the diaper 420 is initially applied and fastened, the caregiver may refasten the diaper 420 by using either the PENTA fastening system 440 or the tab and slot fastening system 483.

In certain embodiments, NT adherent 430 and NT adherend 431 may be disposed on the tab member 485 and slot member 487 in a manner such that the NT adherent 430 and NT adherend 431 may be engaged while the tab member 485 is engaged in the slot 489 of the slot member 487. FIG. 4H depicts such a configuration.

Alternately, NT adherent 430 may be located on a portion of the tab member 485, the slot member 487, a portion of side panels 460, 461, or any combination thereof. Similarly, NT adherend 431 may be located on a portion of the tab member 485, the slot member 487, a portion of side panels 460, 461, or any combination thereof such that the NT adherent 430 may be joined thereto.

Figure 5A:
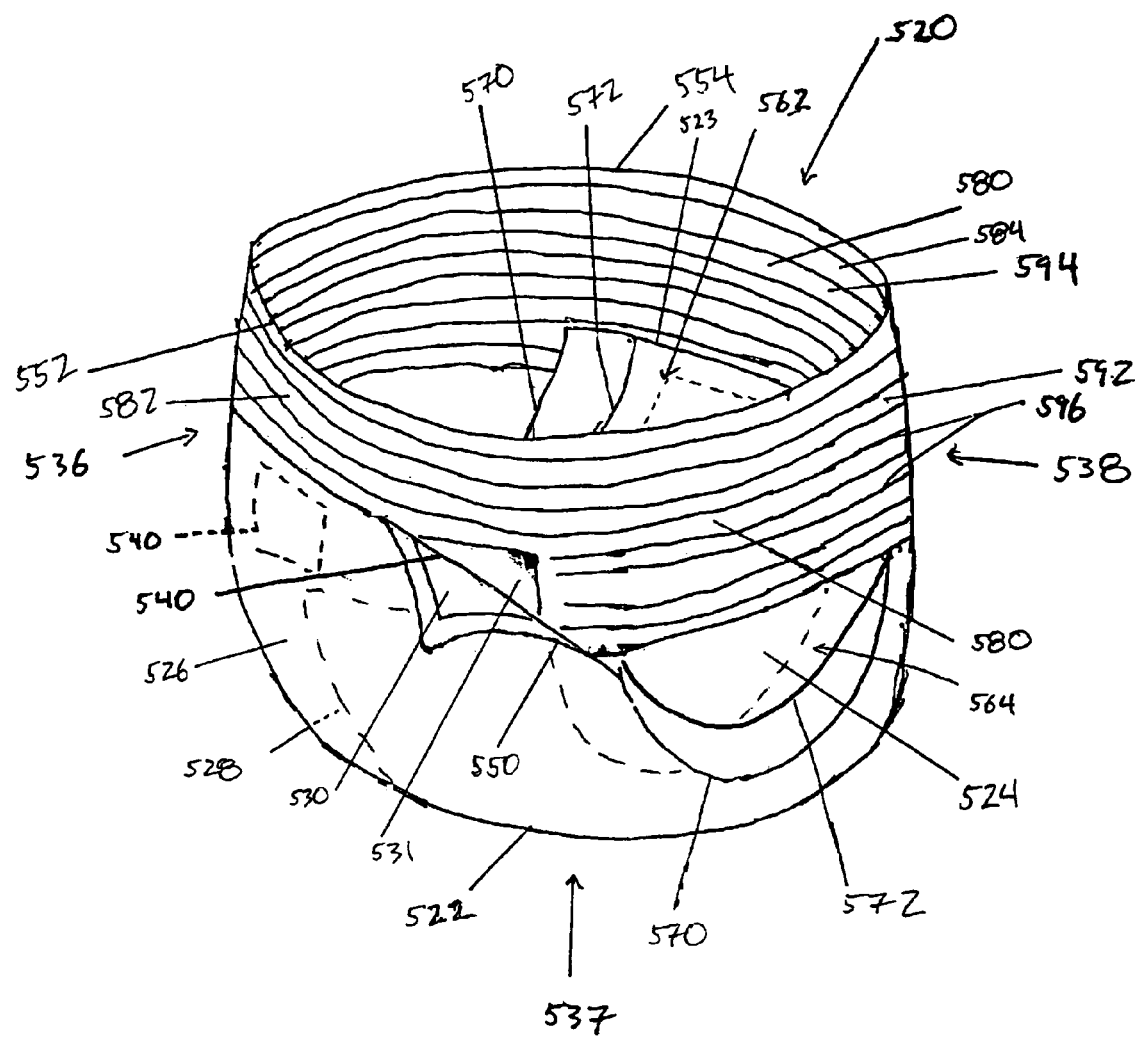
FIG. 5A is a perspective view of another embodiment of an absorbent article with the fastening system partially separated.
Figure 5B:
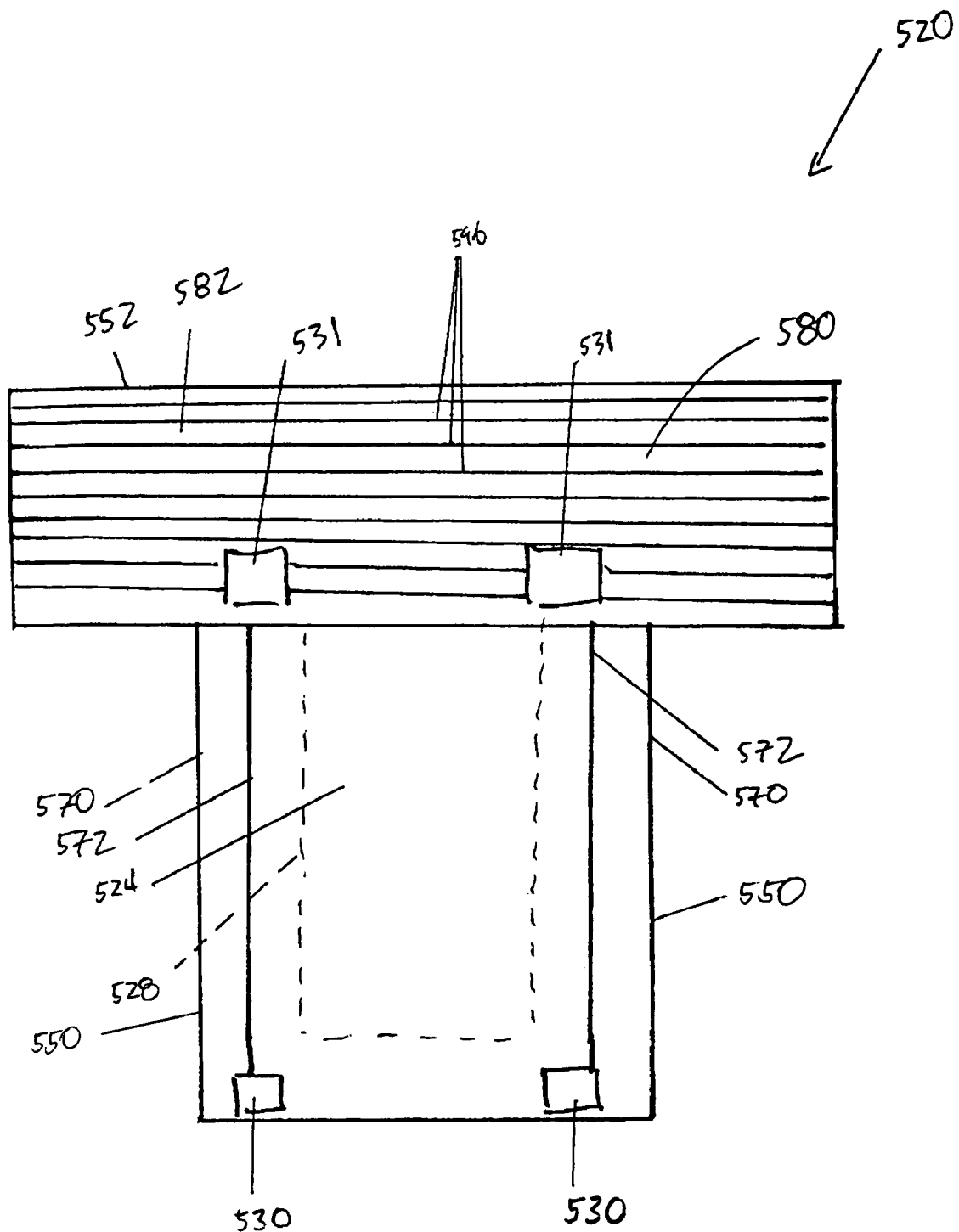
FIG. 5B is a plan view of the absorbent article of FIG. 5A.

FIGS. 5A-B illustrate another embodiment of the present invention with a diaper 520 having a continuous waistband 580 and an absorbent assembly 522 refastenably attached to the waistband 580 by use of a PENTA fastening system 540. FIG. 5A is a perspective view of the diaper 520 with the PENTA fastening system 540 partially separated. FIG. 5B is a plan view of the front of the diaper 520 with the PENTA fastening system 540 fully separated. Unless otherwise noted, elements of diaper 520 may have a similar construction or composition as the like elements as described with reference to the diaper 420 in FIGS. 4A-H. The diaper 520 has a front waist region 536, a back waist region 538 opposed to the front waist region 536, and a crotch region 537 located between the front waist region 536 and the back waist region 538. The periphery of the diaper 520 is defined by the outer edges of the diaper 520 in which side edges 550 lie generally parallel to a longitudinal centerline and the front waist edge 552 and back waist edge 554 lie generally parallel to a lateral centerline of the diaper 520 and extend between the side edges 550.

The absorbent assembly 522 of the diaper 520 may include a liquid pervious topsheet 524, a liquid impervious backsheet 526, and an absorbent core 528 which may be positioned between at least a portion of the topsheet 524 and the backsheet 526. The topsheet 524, the backsheet 526, and the absorbent core 528 may be assembled in a variety of configurations well known in the art including those as described with regard to FIGS. 4A-D. The diaper 520 may have a gasketing cuff 570 and barrier cuff 572.

The waistband 580 encircles the waist of a wearer while the diaper is worn. The waistband 580 forms a waist opening 562. The waistband may be constructed to stretch so as to accommodate a wide size range of wearers and to provide elastic resistance to the dynamic forces encountered during wear of the diaper 520. In one embodiment, the waistband 580 may be an elastic laminate. Construction of elastic laminates is well known in the art.

In one embodiment, the waistband 580 may have an outer layer 592 and an inner layer 594. An elastic member 596 may be interposed between the outer layer 592 and the inner layer 594 to provide elasticity to the waistband 580. The waistband 580 may comprise a variety of suitable materials. Suitable material for the waistband 580 include a wide range of substrates such as plastic films; apertured plastic films; woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. The waistband 580 may comprise a stretchable nonwoven. In a suitable embodiment, the waistband 580 has an inner layer 594 comprising a hydrophobic, non-stretchable nonwoven material, an outer layer 592 comprising a hydrophobic, non-stretchable nonwoven material, and an elastic member 596 there between. In other embodiments, the waistband 580 may comprise the inner layer 594 and/or the outer layer 592 without an elastic member 596 if sufficient elasticity is present in the material which forms the inner layer 594 and/or outer layer 592 (e.g., layer may be an elastic scrim).

The elastic member 596 may comprise one or more elastic elements such as strands or panels extending at least in the transverse direction. The elastic member 596 may be continuously or discontinuously disposed along the transverse width of the waistband. The elastic member 596 may be disposed evenly or disproportionately along the longitudinal length of the waistband 580. The elastic member 596 may be in the form of strands continuously spanning the width of the waistband 580 and may be substantially evenly spaced along the longitudinal length. It may be desirable that no elastic member 596 be provided in the portion of the waistband 580 which overlaps with the absorbent assembly 522; in such cases elastic member 596 may transversely span those portions of the waistband 580 that do not overlap the absorbent assembly 522.

As shown in FIGS. 5A-B, the waistband may include two portions, a front waistband region 582 and a rear waistband region 584. The absorbent assembly 522 may have a lateral rear waist edge 523. The rear waist edge 523 may overlap and may be joined to the rear waistband region 584. In this embodiment, the rear waistband region 584 and the absorbent assembly 522 are permanently joined such that absorbent assembly 522 will remain affixed to the rear waistband region 584 during the normal life of the diaper.

A PENTA fastening system 540, as disclosed above, may be provided to join the absorbent assembly to the front waistband. The PENTA fastening system 540 may include a NT adherent 530 disposed on the garment-facing surface of the front waistband region 582. The fastening system 540 may include a NT adherent 531 disposed on the wearer-facing surface of the absorbent assembly 522. The NT adherent and NT adherent 530, 531 may be positioned in one or more locations on the waistband 580 and absorbent assembly 522. Ideally, when the materials 530, 531 are engaged, the waistband 580 and absorbent assembly 522 form a pair of leg openings 564. As should be appreciated, the NT adherent 530 and NT adherent 531 alternately may be disposed on the absorbent assembly 522 and front waistband region 582, respectively. Furthermore, the NT adherent and NT adherend 530, 531 may be disposed on the body-facing surface and/or the garment-facing surface of the absorbent assembly 422 or the waistband 480.

In another embodiment of the present invention as shown in FIGS. 6A-D, the PENTA fastening system as described above may be included in an article of commerce 620 comprising a bag or overwrap 622 and one or more consumer or commercial goods. A PENTA fastening system 640 may be provided to be seal the bag or overwrap 622 during manufacture. Ideally, the PENTA fastening system 640 may keep the bag or overwrap 622 in a closed configuration until opened by a consumer or other end-user. In one suitable embodiment, the article of commerce 620 comprises an overwrap 622, which is sealed by the PENTA fastening system 640, containing a plurality of consumer goods, such as diapers 650 (which may or may not be the diapers as described above). Overwraps 622 are well-known in the art and provide the benefit of allowing a plurality of diapers 650 to be bound to one another in order to aid in delivery and handling. Generally, the overwrap 622 will encase the plurality of diapers 650 to prevent contamination; however, a partial overwrap 622 may be employed where one or more diapers 650 may be exposed. In the embodiments shown in FIGS. 6A-D, the plurality of diapers 650 may be bound together and covered by a thermoplastic film overwrap 622, such as disclosed in U.S. Pat. No. 5,934,470. Other overwraps 622 are clearly envisioned. For example, the overwrap 622 may comprise a variety of materials including, but not limited to, thermoplastic films, nonwovens, wovens, foils, fabrics, papers, cardboard, elastics, cords, straps, and combinations thereof. Other suitable packages and methods for packaging are disclosed in U.S. Pat. Nos. 5,050,742 and 5,054,619. Furthermore, the article of commerce 620 may contain multiple overwraps. For example, a plurality of diapers 650 may be packaged with a thermoplastic film overwrap and then a plurality of film wrapped diaper may then be overwrapped in a cardboard box or a second thermoplastic film overwrap.

Figure 6A:
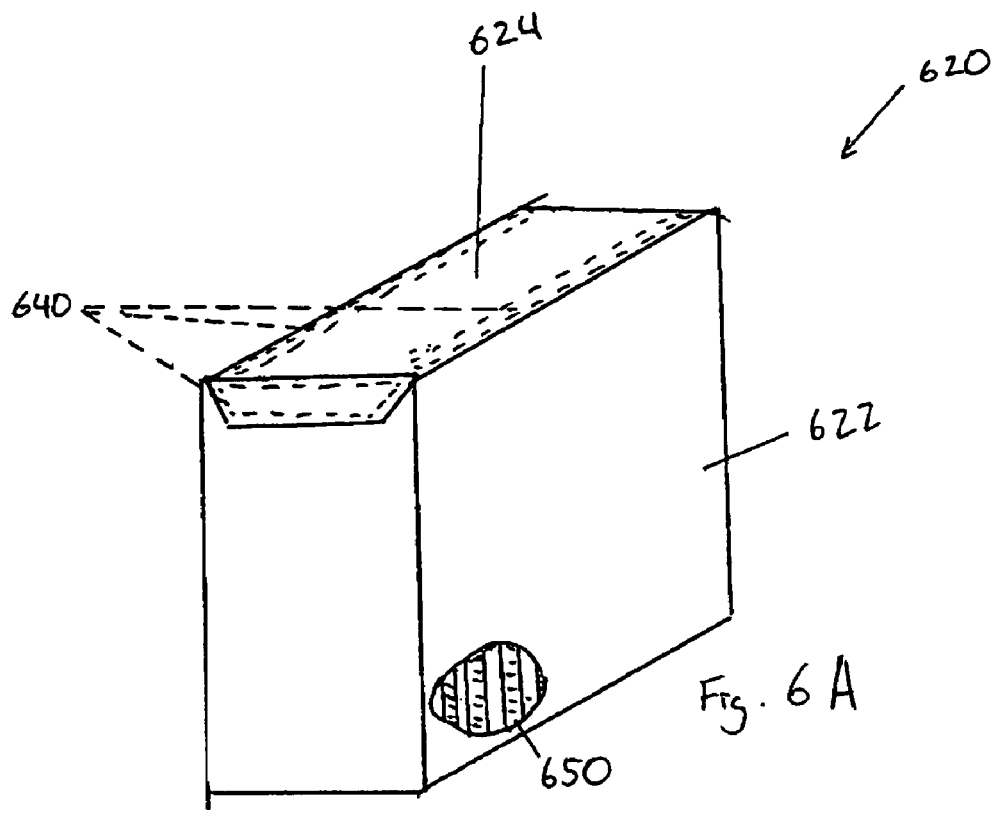
FIG. 6A is a partial cut-away perspective view of an article of commerce having the fastening system.
Figure 6B:
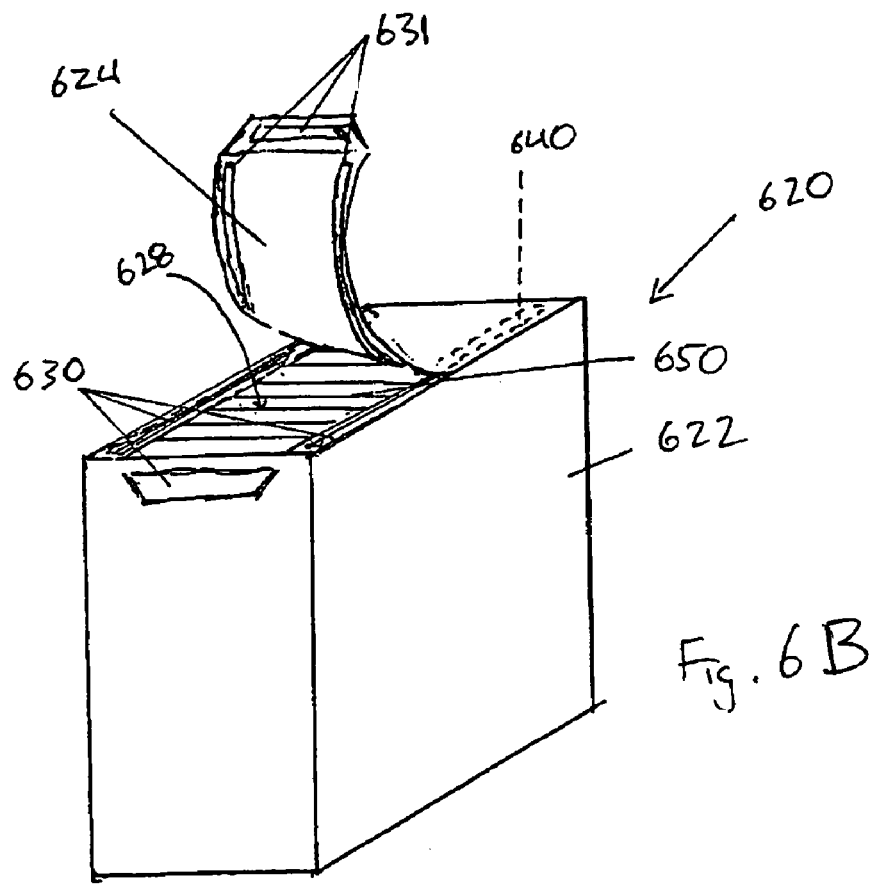
FIG. 6B is a perspective view of the article of commerce of FIG. 6A with the fastening system separated.

The overwrap 622 may include several faces forming a three dimensional void which may be filled by the plurality of diapers 650. A closure flap 624 may extend from the overwrap 622 to cover one or more faces or portions of faces of the overwrap 622. The closure flap 624 may be an extension of the overwrap 622 that releasably covers (i.e., can cover and be manipulated to reveal) some opening 628 in the overwrap 622 that may expose the plurality of diapers 650. The closure flap 624 may be a discrete element releasably or fixedly attached to the overwrap. The closure flap 624 may be of a shape that covers one of the faces of the plurality of diapers 650. The flap 624 includes a PENTA fastening system 640 with a NT adherent 630 disposed on exterior surface of the overwrap 622 and a NT adherend 631 disposed on the interior surface (e.g., surface proximate to the diapers) of the flap 624 or vice versa. FIG. 6A shows the PENTA fastening system 640 in an engaged state, and FIG. 6B shows the PENTA fastening system 640 in a partially separated state. During manufacture, the flap 624 may be positioned to engage the NT adherent 630 and the NT adherend 631. The PENTA fastening system 640 should maintain the flap 624 in a closed position thereby securing the plurality of diapers 650 within the overwrap 622. Ideally, the overwrap 622 will maintain this closed position until a consumer opens the overwrap 622 by separating the PENTA fastening system 640. The PENTA fastening system 640 may be refastenable, which enables a user to open the flap 624 to remove a quantity of diapers and then to refasten the PENTA fastening system 640 to enclose the remaining diapers 650.

In the embodiment shown in FIGS. 6A-B, the flap 624 may be an extension of the overwrap 622 that covers an opening 628 in the overwrap 622. The flap 624 may be permanently affixed to the overwrap 622. The flap 624 may be releasably secured to the overwrap 622 by positioning the fastening system 640 in areas where the flap 624 and overwrap 622 overlap when the flap 624 covers the opening 628. FIGS. 6A-B show the overlapping area as being on opposing edges of the internal face of the flap 624 and along two bands of the overwrap 622 that define opposing sides of the opening 628.

Figure 6C:
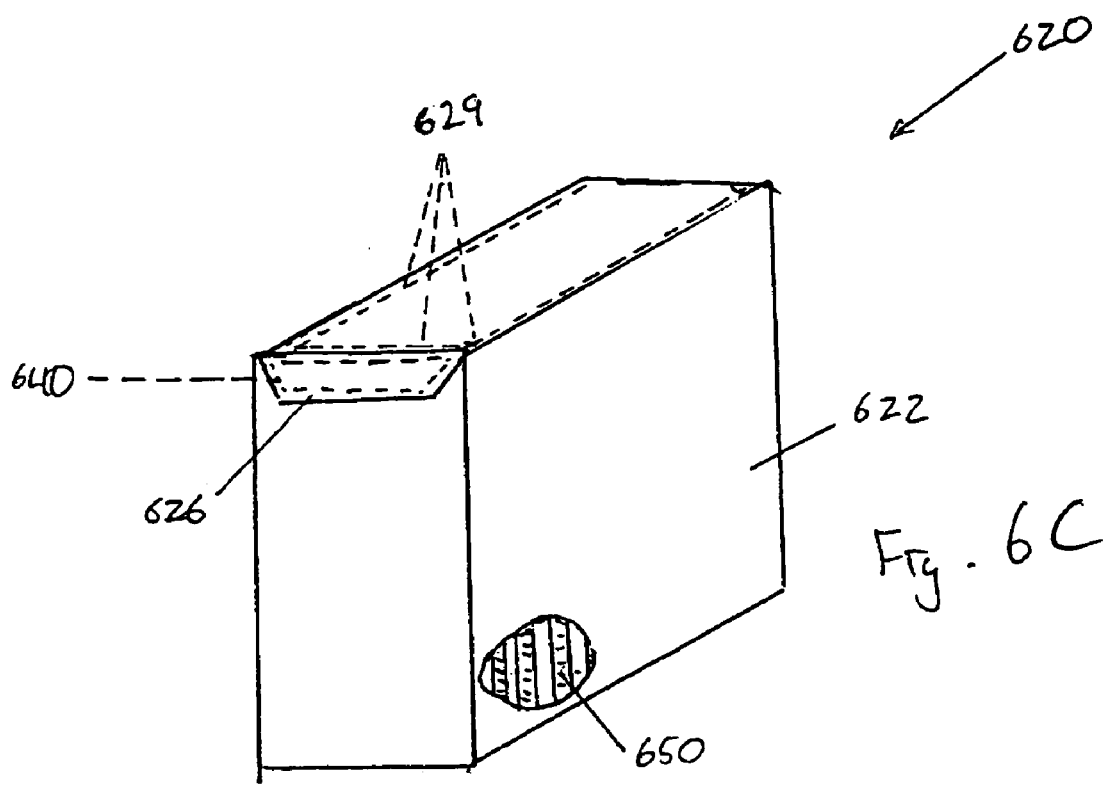
FIG. 6C is a partial cut-away perspective view of another embodiment of an article of commerce having the fastening system.
Figure 6D:
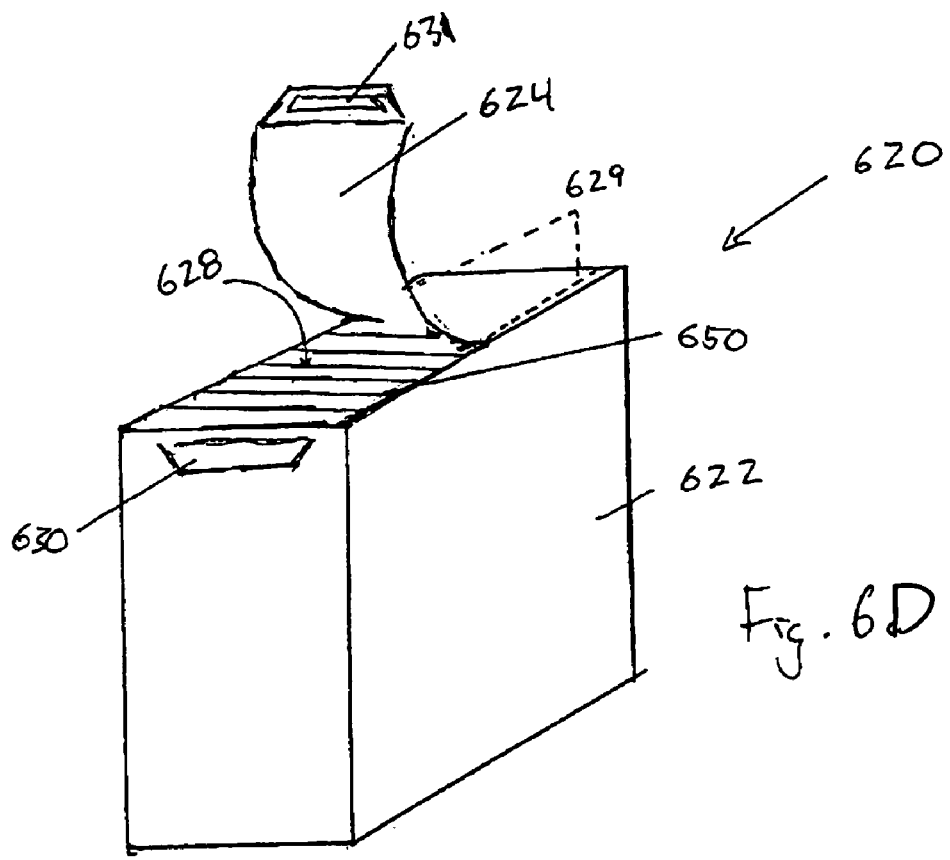
FIG. 6D is a perspective view of the article of commerce of FIG. 6C with the fastening system separated.

In other embodiments, the PENTA fastening system 640 may be coupled with other closure devices that maintain the integrity of the overwrap 622 until use. FIGS. 6C-D illustrate such an example where the overwrap 622 may have one face that may have one or more lines of weakness 629 such as a perforation along one or more edges of the face of the overwrap 622. The overwrap 622 has a tab 626 that may be defined by one or more lines of weakness 629. The tab 626 is affixed to the overwrap 622 by a PENTA fastening system 640. The exterior surface of the overwrap 622 may have a NT adherent 630 disposed thereon. The exterior surface of the overwrap 622 may be overlapped by the tab 626 which may have a NT adherend 631 disposed thereon or vice versa. The overwrap 622 may be manufactured such that the tab 626 is secured to the overwrap 622. The flap 624 may be formed by tearing the overwrap 622 along the lines of weakness 629 to form an opening 628 to the plurality of diapers 650. FIG. 6D shows the flap 624 partially separated along the lines of weakness 629 and with the fastening system 640 separated. Ideally, the flap 624 will remain attached along at least one edge to the overwrap 622. This can be achieved by ensuring that the lines of weakness 629 do not define an enclosed area. Otherwise, the flap 624 may be torn from the overwrap 622. The flap 624 may be re-secured to the overwrap 622 by refastening the fastening system 640. The flap 624 may be opened and closed a number of times in order to access the plurality of diapers 650 within the overwrap. As can be appreciated by one of ordinary skill, the relative size, shape, and location of the flap 624 may be readily modified.

Figure 7A:
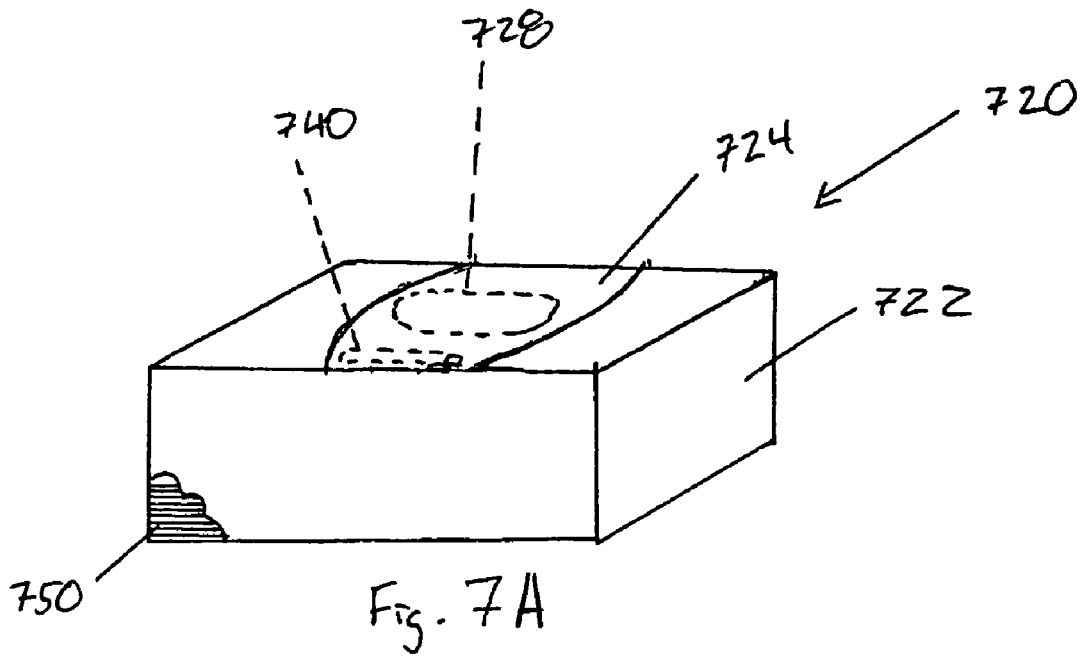
FIG. 7A is a partial cut-away perspective view of another embodiment of an article of commerce having the fastening system.
Figure 7B:
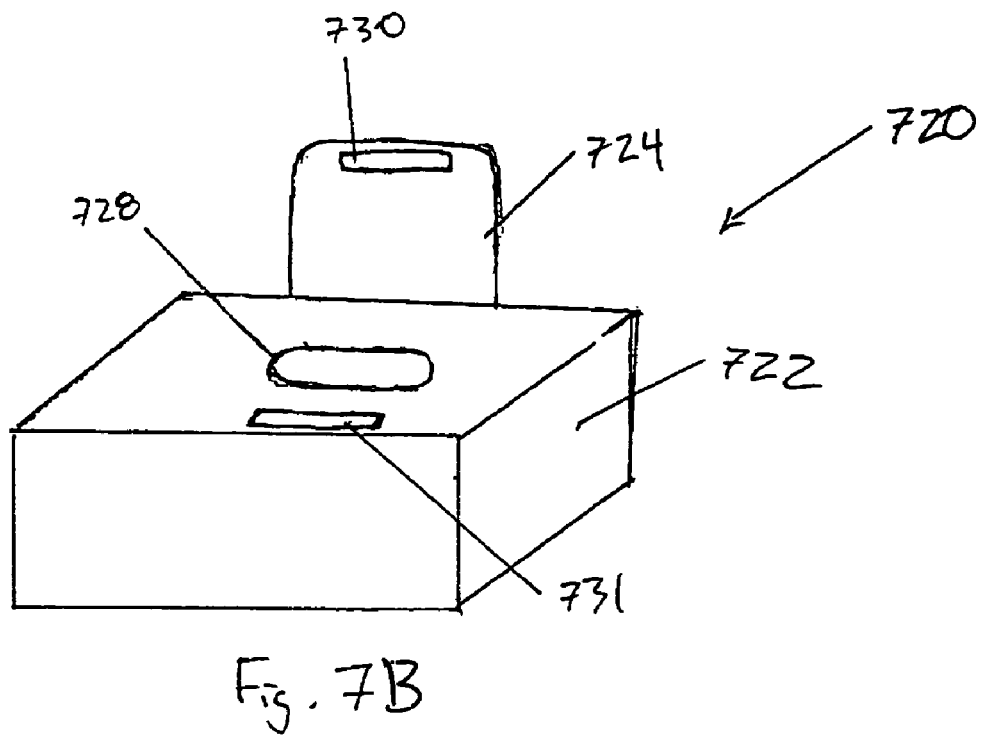
FIG. 7B is a perspective view of the article of commerce of FIG. 7A with the fastening system separated.

In another embodiment of an article of commerce 720 as shown in FIGS. 7A-B, a plurality of wipes 750 may be packaged within an overwrap 722. The overwrap 722 may be made from a moisture impervious material such as polymer films, metallic foils, and the like. Furthermore, the overwrap 722 may be a rigid plastic structure such as a tub which is commonly available. Wipes, tissues, and the like may be contained within the overwrap 722. Wipes 750 packaged within an overwrap 722 are commonly used to refill a permanent, rigid container. In certain embodiments, the overwrap 722 may include a recloseable dispensing mechanism allowing access and removal of one or more wipes 750. A flap 724 may extend from the face of the overwrap 722 and may cover an opening 728 in the overwrap 722. One flap 724 or edges of the flap 724 may be releasably affixed to the overwrap 722 by use of a PENTA fastening system 740. A NT adherent 730 may be disposed on the interior surface of the flap 724 and a NT adherend 731 may be disposed on the exterior surface of the overwrap 722 or vice versa. During manufacture the NT adherent 730 and the NT adherend 731 are engaged thereby securing the flap 724 to the overwrap 722 and covering the opening 728. In some embodiments, the PENTA fastening system 740 may partially or fully encircle the opening 728 so a relatively moisture impervious seal is formed. In use, the flap 724 may be released from the overwrap 722 by separating the NT adherent 730 from the NT adherend 731. The wipes 750 may be accessed and removed through the opening 728. The PENTA fastening system 740 may then be refastened thereby re-closing the flap 724 and protecting the remaining wipes 750 within the overwrap 722.

Test Methods

For each of the sample preparations described below, the adherent and adherend must be handled with care to avoid contact with hands, skin, or other contaminating surfaces. Clean sheets of untreated paper may be used to protect the surfaces of the adherent and adherend during the sample preparation.

T-Peel Test

This method is used to determine the T-Peel strength of the bond formed in a pre-fastened system between an adherent and an adherend after aging and after refastening the aged fastening system three times.

Sample Preparation—The sample preparation for T-peel test will vary based on whether the material is available as a discrete web or is incorporated in a product.

Figure 8A:
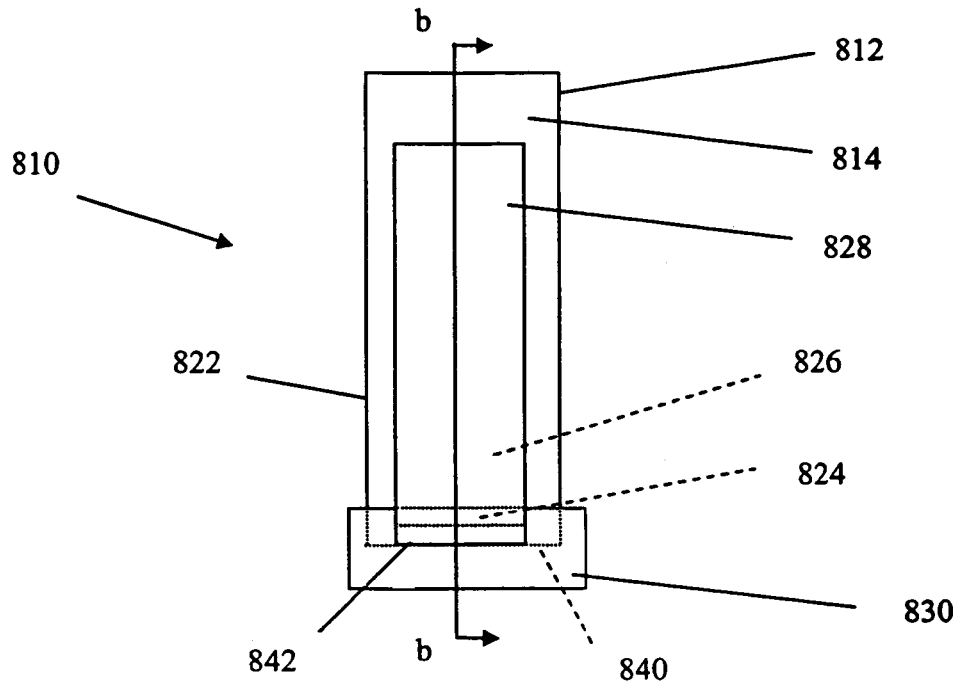
FIG. 8A is a plan view of a representative sample for the T-Peel test.
Figure 8B:
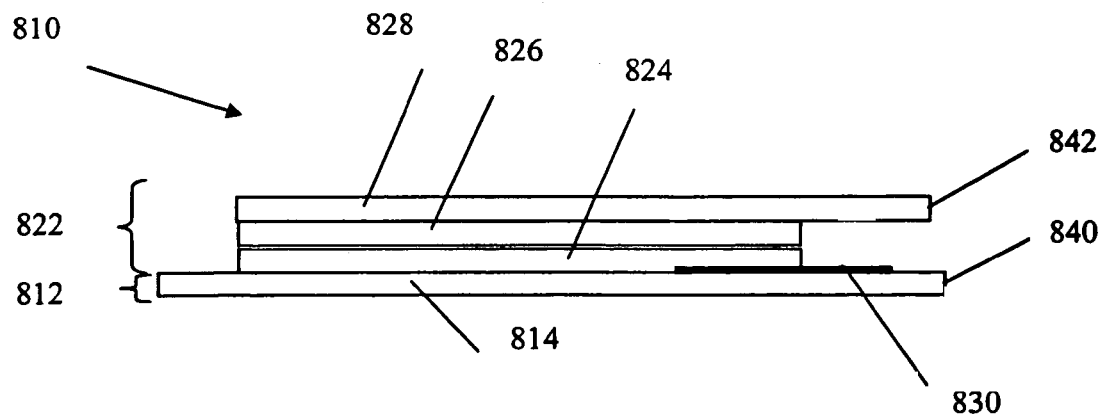
FIG. 8B is a sectional view of the sample of FIG. 8A taken along sectional line b-b.

For materials as a discrete web: FIGS. 8A-B illustrate a bonded sample 810 formed according to the directions provided below. FIG. 8B is a cross-sectional view taken along sectional line b-b of FIG. 8A.

For a receiving sample 812 having a proximal edge 840, an adherend 814 is resized using cutting dies to create rectangular receiving samples with the dimensions of about 3.5 cm (1.4") wide and about 20 cm (7.9") long. In instances where the adherend 814 is elastomeric, the receiving sample is backed with like sized piece of poly(ethylene terephthalate) film or paper using double sided tape.

For the engaging sample 822, a 2.54 cm (1") wide×10.80 cm (4") long piece of an adherent 824 is bonded in a face-to-face relationship to a similarly sized piece of double-sided tape 826 (such as FT 239 available from Avery Dennison Corp., Painesville, Ohio or 9589 available from 3M, St. Paul, Minn.). The adherent 824 and double-sided tape 826 are joined to be substantially coterminous. The adherent 824 is to be wrinkle free. It should be appreciated that the adherent/double sided tape laminate can be created with larger sized materials and then resized to 2.54 cm×10.80 cm. The other side of the double side tape 826 is bonded onto an approximately 2.54 cm×15 cm (1"×5.9") piece of 2 mil (0.05 mm) poly(ethylene terephthalate) (PET) film 828. The PET 828 is bonded to be coterminous with three edges of the adherent/double sided tape laminate leaving a proximal edge 842 of the PET unbonded to the adherent/double sided tape laminate.

The PET film 828 is used as a backing to prevent stretching of the adherent 824 during testing.

Figure 8C:
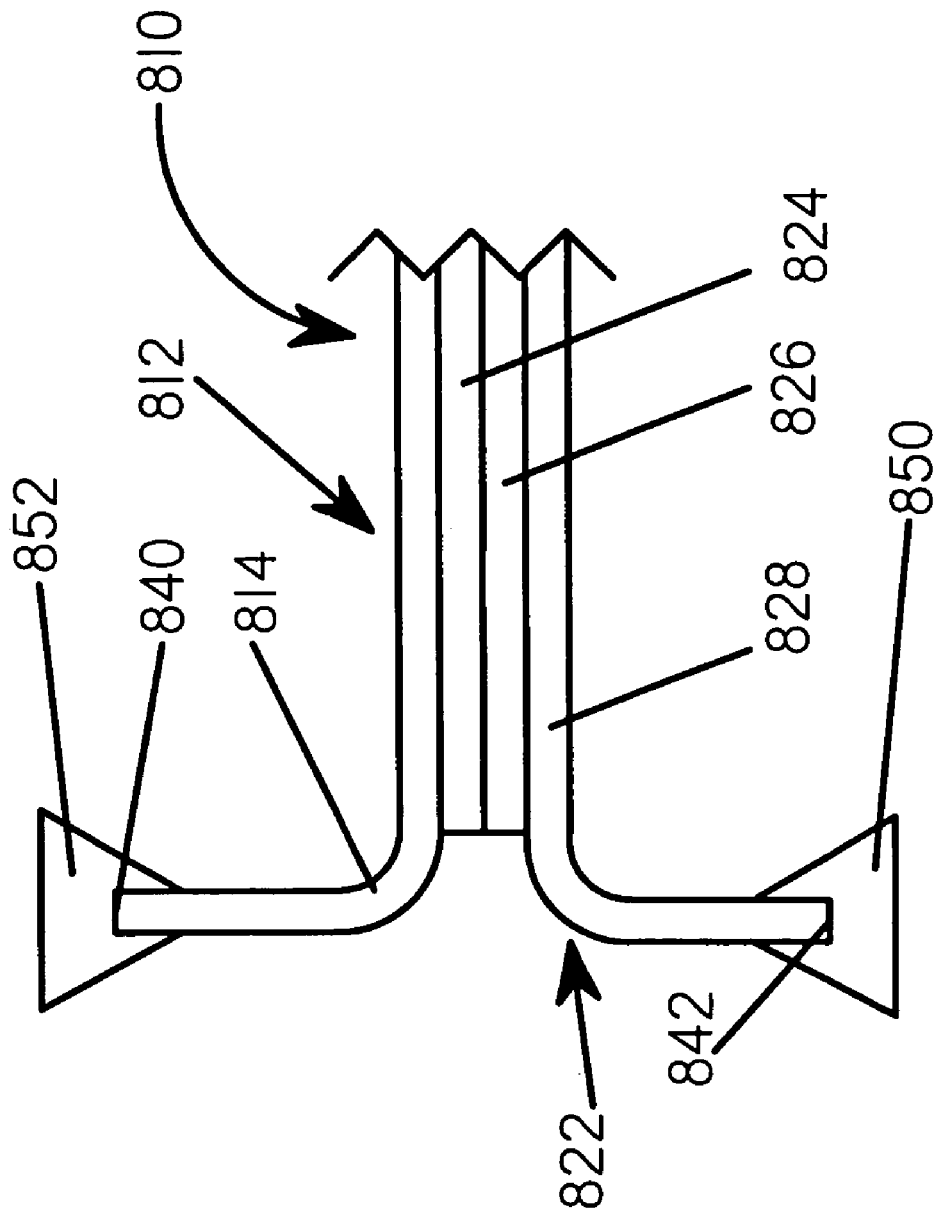
FIG. 8C is a partial cross-sectional view of the sample of FIG. 8A in a set of tensile tester grips.

The engaging sample 822 is bonded to the receiving sample 812. Bonding is to be performed on a flat, clean, rigid surface such as a countertop. The engaging sample 822 is applied to the receiving sample 812 so as to avoid wrinkles. The adherend 814 fully overlaps the adherent 824. The adherent 824 is centered on the adherend 814 with the longitudinal edges of the adherent 824 being substantially parallel to the longitudinal edges of the adherend 814. The proximal edge 840 of the receiving sample 812 is aligned with the proximal edge 842 of the PET 828. The receiving sample 812 and engaging sample 822 should each extend at least 25 millimeters beyond the bonded portion of the samples such that the proximal edge 840 of the receiving sample 812 and the proximal edge 842 of the PET 828 can be easily placed in the test instrument's grips 850 and 852 (as shown in FIG. 8C). If bonded sample 810 is to be aged, a small piece of release paper 830 (such as a double sided silicone coated paper available as supplier code HV100-473/473 from Fox River Associates, LLC., Geneva, Ill.) is placed between the adherend 814 (adjacent the proximal edge 840) and the adherent 824 (adjacent the proximal edge 842). The release paper 830 should not be inserted more than a few millimeters between the adherend 814 and the adherent 824 (i.e., no more than 10% of the total bonded length). The bonded sample 810 is rolled with a 4.5 pound (2 kg) HR-100 ASTM 80 shore rubber-faced roller. Two full strokes (i.e., back and forth) are applied to the sample at a speed of approximately 10 mm/sec. The bonded area should be approximately 1" (2.54 cm) wide by 4" long (10.80 cm) (i.e., the same area as the engaging sample). The bonded sample 810 is subjected to an accelerated aging process at a temperature of 60° C. and a pressure of 0.8 N/cm² for at least 3 days prior to testing to provide an Aged T-Peel Force. (However, some bonded samples may additionally be tested after aging for longer periods of time such as 7 days or shorter periods of time such as 6 hours.)

A skilled artisan should recognize that bonded specimens of other dimensions may be used in the T-Peel Method. The dimensions of the receiving and engaging members may vary from those listed above; however, the effective bonding area should be used to normalize the resultant T-Peel force recorded per inch of bonded width (i.e., the bonded width being the width of the bonded area measured substantially parallel to the grip width once the sample is mounted in the tensile tester).

Materials incorporated in a product: Materials that are pre-bonded in the product are taken as having been aged. As a result, these materials are not subjected to accelerated aging to simulate real environmental aging. To perform the T-peel test, the material is cut from the product so as to isolate the adherend and adherent, if possible. However, if the adherend and/or adherent are joined to other materials in a face-to-face configuration, the face-to-face configuration between the adherend and the other material or adherent and the other material should be maintained. Removal of the materials from the product should be done to preserve the integrity of the materials (e.g., adherend and adherent should not be permanently deformed or should not be debonded from each other). Before loading the samples for T-peel test, the receiving and engaging surfaces should be separated approximately 1-5 mm to initiate the peeling. The portion of the sample including the adherend is the receiving sample 812, and the portion of the sample including the adherent is the engaging sample 822. The receiving sample 812 and engaging sample 822 should each extend at least 25 millimeters beyond the bonded portion of the samples such that the proximal edge 840 of the receiving sample 812 and the proximal edge 842 of the engaging sample 822 can be easily placed in the test instrument's grips 850 and 852. If needed, an additional length of 2 mil PET film may be attached to the proximal edges 840 and 842 using double sided tape. The T-peel test should be performed on the bonded materials as described in the method below. A skilled artisan should recognize that peel angle can affect the peel force. During peeling, the peel angle should be maintained around 180 deg. Furthermore, if the adherent or adherend are elastomeric, the adherent or adherend must be backed with a similar sized sheet of 2 mil (0.05 mm) PET film in order to prevent stretching of the tested substrate.

If the product is not pre-engaged, the materials are cut from the product and sample preparation would be similar to the method presented above for a sample in a film form. These samples would need aging after engagement. If the width of the material is less than 1" then the weight (during aging) should be chosen such that combining pressure is 0.8 N/cm2. The average load calculated in peel force test should be normalized by the width of the fastener (in inches).

Refastened samples—Any of the above mentioned bonded samples (e.g., materials in a discrete film form after accelerated aging or material in a product) may be refastened. The bonded sample 810 is debonded using the tensile tester and following the Test Conditions for the T-Peel Test as provided for below (e.g., crosshead speed of 12 inches/minute). The adherent 824 and adherend 814 are refastened in a configuration substantially similar to the configuration in which they were originally attached while avoiding wrinkles. The refastened sample is rolled with a 4.5 pound (2 kg) HR-100 ASTM 80 shore rubber-faced roller. Two full strokes (i.e., back and forth) are applied to the sample at a speed of approximately 10 mm/sec (i.e., rolling should take approximately 40 seconds. After 1 minute of dwell time, the T-Peel Test is performed. This is the first refastened T-Peel force. This procedure may be repeated as needed to yield sequential refastened T-Peel forces (i.e., a second refastened T-Peel force, a third refastened T-Peel force, etc.).

Test Conditions—The T-Peel test method is performed in a controlled room at 22° C.+/−2° C. and RH 50%+/−10%. Suitable instruments for this test include tensile testers commercially available from Instron Engineering Corp., Canton, Mass. (e.g. Instron 5564) or from MTS Systems Corp., Eden Prairie, Minn. (e.g. Alliance RT/1 or Sintech 1/S). The following procedure illustrates the measurement when using the Instron 5564. The instrument is interfaced with a computer loaded with the Instron® Merlin™ Material Testing Software which controls the testing parameters, performs data acquisition and calculation, and provides graphs and data reports. The instrument is configured with a data acquisition speed of 50 Hz. Any resulting graphs are plotted using the Average Value (integral) setting on the instrument. A load cell is selected so that the forces to be measured will be between 10% and 90% of the capacity of the load cell or the load range used (e.g., typically, a 10N to 100N load cell). The instrument is calibrated to an accuracy of at least 1% and, ideally, less than 0.1% according to the manufacturer's instructions. The instrument has two grips: a stationary grip 850 and a movable grip 852. The grips 850, 852 used are wider than the sample; typically, 2 inch (5.08 cm) wide grips are used. The grips 850, 852 are air-actuated grips and designed to concentrate the entire gripping force along a plane perpendicular to the direction of testing stress. The distance between the lines of the gripping force (i.e., gauge length) is set to 1" (2.54 cm). The load reading on the instrument is zeroed to account for the mass of the fixture and grips. The bonded sample 810 is mounted into the grips 850, 852 as shown in the partial cross-sectional view of FIG. 8C. The bonded sample 810 is mounted so that the proximal edge 840 of the receiving sample 812 is in the movable grip 852 and the proximal edge 842 of the engaging sample 822 is in the stationary grip 850. The bonded sample is mounted such that there is a minimum amount of slack in the receiving sample 812 or engaging sample 822 between the grips. The load cell is zeroed.

The receiving sample 812 is separated from the engaging sample 824 using a crosshead speed of 12 inches/min (305 mm/min). An average load is calculated as the average load between about 1" (about 25 mm) and about 3.5" (about 88 mm) displacement. For samples that do not meet the dimensions provided in the Sample Preparation, the average load is calculated from the loads acquired from the crosshead extension between about 25% to about 87.5% of the sample length. For example, if the sample is 6 inches long, the average load is calculated between about 1.5 inches and about 5.24 inches of crosshead extension. The average load is normalized to a width of 1" (2.54 cm) as follows: normalized load=average load÷initial bond width in inches.

Dynamic Shear Test Method

This method is used to determine the shear strength of the bond formed between an adherent and an adherend after aging and after refastening three times. The dynamic shear test method is performed in the same environmental conditions and with the same instrument as disclosed in the T-Peel Test.

Sample Preparation—The sample preparation for T-peel test will vary based on whether the material is available as a discrete web or is incorporated in a product.

Figure 9A:
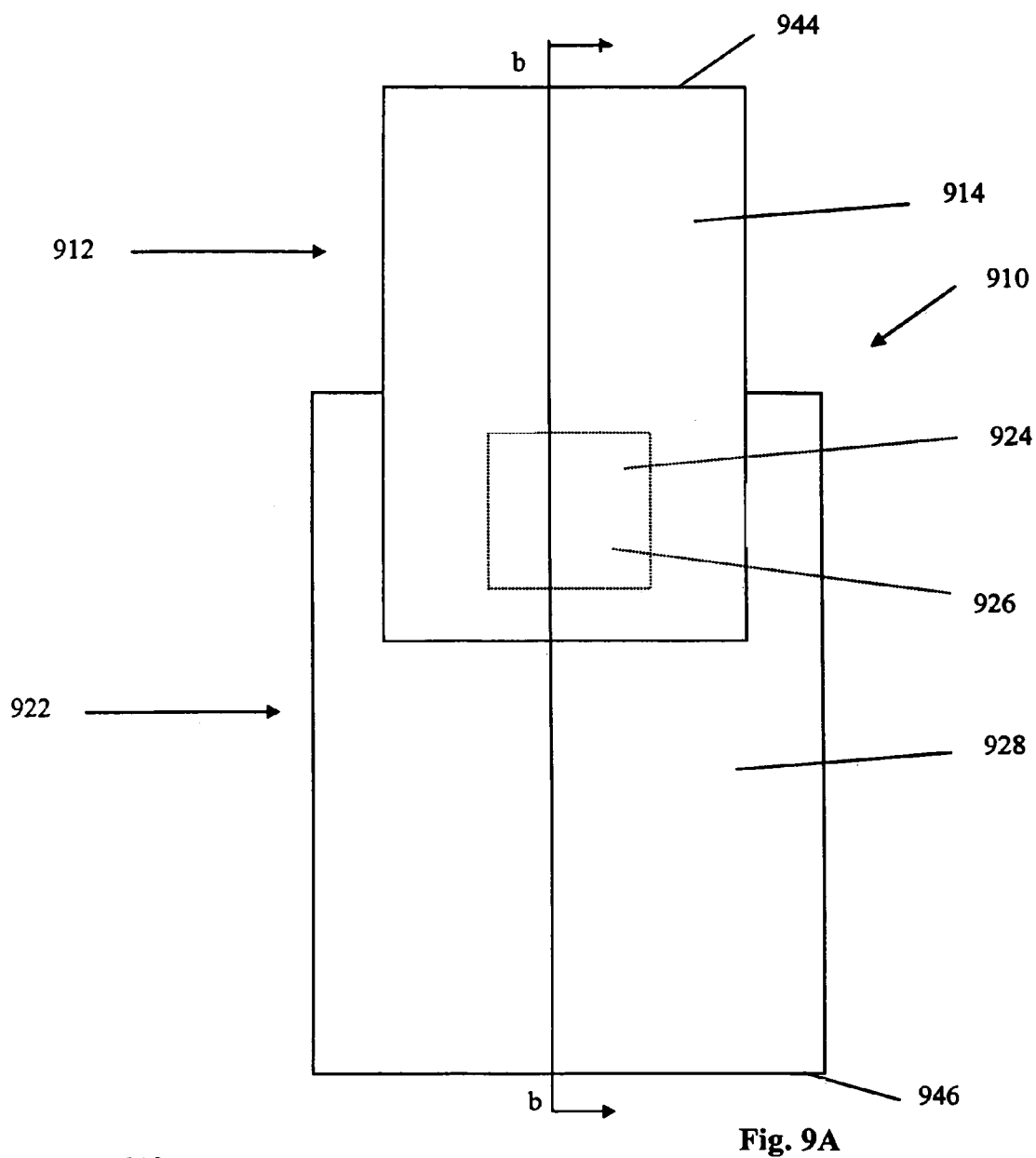
FIG. 9A is a plan view of a representative sample for the Dynamic Shear test.
Figure 9B:
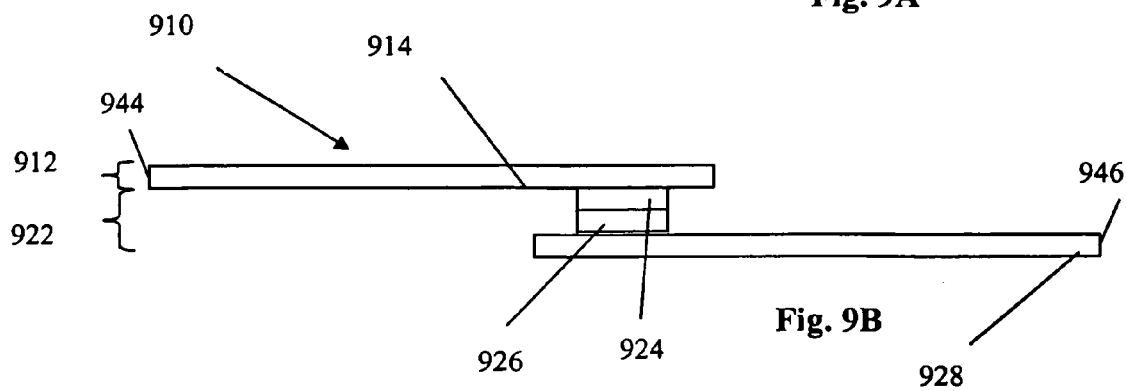
FIG. 9B is a sectional view of the sample of FIG. 9A taken along sectional line b-b.

For materials as a discrete web: FIGS. 9A-B illustrate a bonded sample 910 formed according to the directions provided below. FIG. 9B is a cross-sectional view taken along sectional line b-b of FIG. 9A.

For a receiving sample 912 having a distal edge 944, an adherend 914 is resized using cutting dies to create rectangular receiving samples with the dimensions of about 3.5 cm (1.4") wide and about 20 cm (7.9") long. In instances where the adherend 914 is the same as an adherent 924, the receiving sample is backed with a like sized piece of poly(ethylene terephthalate) film or paper using double sided tape.

For the engaging sample 922, an approximately 2.54 cm×2.54 cm (1"×1") piece of the adherent 924 is bonded in a face-to-face relationship to a similarly sized piece of double-sided tape 926 (such FT 239 available from Avery Denninson Corp., Painesville, Ohio or 9589 available from 3M, St. Paul, Minn.). The adherent 924 and double-sided tape 926 are joined to be substantially coterminous. The adherent 924 is to be wrinkle free. It should be appreciated that the adherent 924/double sided tape 926 laminate can be created with larger sized materials and then resized to about 2.54 cm×2.54 cm. The other side of the double side tape 926 is bonded to a 2"×6" stainless steel plate 928 such that one side of the adherent 924/double sided tape 926 is approximately 0.5" from a 2" wide edge of plate 928. The plate 928 has a distal edge 946 opposite the edge which is adjacent the adherent 924/double sided tape 926 laminate. The adherent 924/double sided tape 926 should be centered along the width of the plate 928.

The receiving sample 912 is bonded on the engaging sample 922 such that the adherend 914 fully overlaps the adherent 924. The receiving sample 912 is applied so as to avoid wrinkles. The edges of the receiving sample 912 and the edges of the engaging sample 924 are substantially parallel to each other. The receiving sample 912 is bonded to the engaging sample 922 such that the receiving sample 912 extends beyond the plate 928. The bonded sample 910 is configured such that the distal edge 944 of the receiving sample 912 and the distal edge 946 of the plate 928 are opposite one another. The bonded sample 910 is rolled with a 4.5 pound (2 kg) HR-100 ASTM 80 shore rubber-faced roller. Two full strokes (i.e., back and forth) are applied to the sample at a speed of approximately 10 mm/sec. The bonded area should be approximately 1" (2.54 cm) by 1" (2.54 cm). The bonded sample 910 is subjected to an accelerated aging process at a temperature of 60° C. and a pressure of 0.8 N/cm$^2$ for at least 3 days prior to testing to provide an Aged T-Peel Force. (However, some bonded samples may additionally be tested after longer periods of time such as 7 days.)

A skilled artisan should recognize that bonded specimens of other dimensions may be used in the Dynamic Shear Test Method. The dimensions of the receiving and engaging members may vary from those listed above; however, the effective bonding area should be used to normalize the resultant Dynamic Shear force recorded per square inch of bonded area.

Materials incorporated in a product: Materials that are pre-bonded in the product are taken as having been aged. As a result, these materials are not subjected to accelerated aging to simulate real environmental aging. To perform the dynamic shear test, the material is cut from the product so as to isolate the adherend and adherent, if possible. However, if the adherend and/or adherent are joined to other materials in a face-to-face configuration, the face-to-face configuration between the adherend and the other material or adherent and the other material should be maintained. Removal of the materials from the product should be done to preserve the integrity of the materials (e.g., adherend and adherent should not be permanently deformed or debonded). The adherent is attached to a 2"×6" stainless steel plate to form an engaging sample. The adherend (already engaged with the adherent) should have a distal edge that extends at least 25 millimeters from the bonded portion of the adherent and adherend such that the distal edge can be easily inserted into the test instrument's grip 952. If the distal edge of the adherend does not extend at least 25 mm, an additional length of 2 mil PET film may be attached to the distal edge of the adherend using double sided tape. The Dynamic Shear test should be performed on the bonded materials as described in the method below.

If the product is not pre-engaged, the materials are cut from the product and sample preparation would be similar to the method presented above for a sample in a film form.

Refastened samples—Any of the above mentioned bonded samples (e.g., materials in a discrete film form after accelerated aging or material in a product) may be refastened. A refastened sample is prepared as follows. A bonded sample 910 is manually debonded by peeling the receiving sample 912 from the engaging sample 922. The adherent 924 and adherend 914 are refastened in a configuration substantially similar to the configuration in which they were originally attached while avoiding wrinkles. The bonded sample 910 is configured such that the distal edge 944 of the receiving sample 912 is remote from the distal edge 946 of the plate 928.

The refastened sample is rolled with a 4.5 pound (2 kg) HR-100 ASTM 80 shore rubber-faced roller. Two full strokes (i.e., back and forth) are applied to the sample at a speed of approximately 10 mm/sec. The refastened sample is allowed to sit for 1 minute of dwell time. Debonding and refastening may be repeated to yield a second refastening, third refastening, etc. The refastened sample may be tested to provide a Dynamic Shear.

Figure 9C:
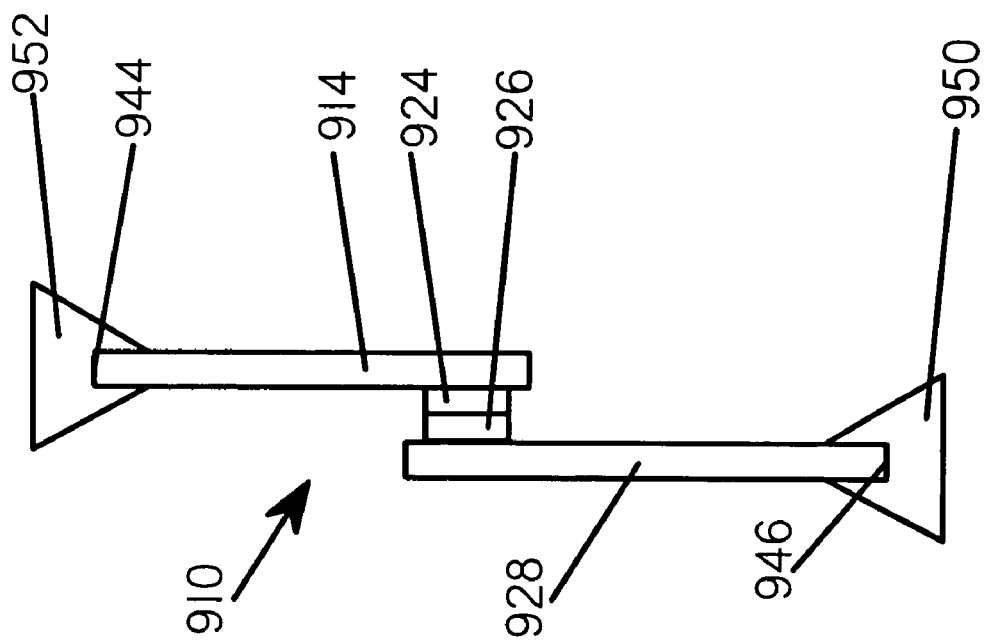
FIG. 9C is a cross-sectional view of the sample of FIG. 9A in a set of tensile tester grips.

Test Conditions—The Dynamic Shear test method is performed in a controlled room at 22° C.+/−2° C. and RH 50%+/−10%. The tensile tester is the same as used in the T-Peel test. A load cell is selected so that the forces to be measured will be between 10% and 90% of the capacity of the load cell or the load range used (e.g., typically, a 100N to 250N load cell). The instrument is calibrated to an accuracy of at least 1% and, ideally, less than 0.1% according to the manufacturer's instructions. The tensile tester has two grips: a stationary grip 950 and a movable grip 952. FIG. 9C is a cross-sectional view of the bonded sample 910 mounted in two grips 950, 952 of the tensile tester. The grips are wider than the adherend 914 or adherent 924 (e.g., typically, about 1 to about 2 inch wide (2.54-5.08 cm)). The grips 950, 952 are air-actuated grips and designed to concentrate the entire gripping force along a plane perpendicular to the direction of testing stress. The distal edge 946 of the metal plate 928 is mounted into the stationary grip 950. The distal edge 944 receiving sample 912 is mounted into the movable grip 952. The bonded sample is to be mounted into the grips 950, 952 so that there is a minimum amount of slack and the load measured is less than 0.5 N. The distance between the lines of the movable grip 952 and the proximate edge of the bond site is about 1.3 inches (about 3.3 cm). The load reading on the instrument is zeroed.

The receiving sample 912 is separated from the engaging sample 924 using a crosshead speed of 12 inches/min (305 mm/min) until the two samples are completely disengaged or one of the bonded sample 910 fails (e.g., the engaging sample tears, receiving sample tears, or the sample debonds at an interface other than of that between the engaging sample and the receiving sample). If the bonded sample fails at any location other than the interface between the adherend and adherent prior to reaching a maximum load of at least 20 N/in$^2$, the data is to be discarded and another sample must be run using a backing material to prevent the sample form tearing and/or using a stronger double sided tape.

The Maximum Load is recorded and normalized to Newtons per inch$^2$ as follows: normalized load=measured load÷bonded area in inches squared.

Shear Hang Time Test Method

This method is used to determine the shear resistance, measured in time, of the bond formed between an adherent and an adherend (after aging and after refastening the aged sample three times) when the bond is subjected to a load in controlled temperature environments. This test is derived from FINAT Test Method No. 8, the European Association for the Self Adhesive Tape Industry (AFERA) Test Method No. 4012, and ASTM-D Test Method No. 6463.

Sample Preparation—The sample preparation for Shear Hang Time test will vary based on whether the material is available as a discrete web or is incorporated in a product.

For materials as a discrete web: FIGS. 10A-B illustrate a bonded sample 1010 formed according to the directions provided below. FIG. 10B is a cross-sectional view taken along sectional line b-b of FIG. 10A For a receiving sample 1012 having a proximal edge 1040 and a distal edge 1044, an adherend 1014 is resized using cutting dies to create a rectangular sample with the dimensions of about 3.5 cm×about 7.5 cm (1.4"×3.0"). The adherend 1014 is backed with a like sized backing sheet 1015 of (polyethylene terephthalate) film or paper. The backing sheet 1015 must be positioned and sized so as to not interfere with the adherend 1014 to the adherent 1024 interface.

For the engaging sample 1022, an approximately 1.3 cm×2.54 cm (0.5"×1") piece of an adherent 1024 is bonded in a face-to-face relationship to a similarly sized piece of double-sided tape 1026 (such as FT 239 available from Avery Denninson Corp., Painesville, Ohio or 9589 available from 3M, St. Paul, Minn.). The adherent 1024 is to be wrinkle free. It should be appreciated that the adherent 1024/double sided tape 1026 laminate can be created with larger sized materials and then resized to 1.3 cm×2.54 cm. The other side of the double side tape 1026 is bonded to a test panel 1028 having a proximal edge 1042 and a distal edge 1046. The double side tape 1026 is bonded adjacent the proximal edge 1042 of the test panel 1028. The test panel 1028 is ideally made from steel (ASTM A666 specification); alternately, the test panel 1028 may be made from a corrugated cardboard with a thickness of at least about 3-4 mm. The adherent 1014 is bonded onto the adherent 1024. The bonded sample 1010 is then rolled with a 4.5 pound (2 kg) HR-100 ASTM 80 shore rubber-faced roller. Two full strokes (i.e., back and forth) are applied to the sample 1010 at a speed of approximately 5 mm/sec. The bonded area should be approximately 2.54 cm×1.3 cm (0.5"× 1.0"). The bonded sample 1010 is subjected to an accelerated aging process at a temperature of 60° and a pressure of 0.8 N/cm$^2$ for at least 3 days prior to testing.

A skilled artisan should recognize that bonded specimens of other dimensions may be used in the Shear Hang Time Test Method. The dimensions of the receiving and engaging members may vary from those listed above. However, if the bonded area exceeds approximately 2.54 cm×1.3 cm (0.5"× 1.0"), the sample should be resized to yield a bonded area of 2.54 cm×1.3 cm (0.5"×1.0").

Materials incorporated in a product: Materials that are pre-bonded in the product are taken as having been aged. As a result, these materials are not subjected to accelerated aging to simulate real environmental aging. To perform the dynamic shear test, the material is cut from the product so as to isolate the adherend and adherent, if possible. However, if the adherend and/or adherent are joined to other materials in a face-to-face configuration, the face-to-face configuration between the adherend and the other material or adherent and the other material should be maintained. Removal of the materials from the product should be done to preserve the integrity of the materials (e.g., adherend and adherent should not be permanently deformed and should not be debonded from each other). The adherent is attached via double sided tape to a test panel 1028 to form an engaging sample. The adherend (already engaged with the adherent) should have a distal edge that extends at least 50 millimeters from the bonded portion of the adherent and adherend such that the distal edge can be easily be folded over to form a loop 1062. If the distal edge does not extend at least 50 mm, an additional length of 2 mil PET film may be attached to the distal edge 1044 using double sided tape. The shear hang test should be performed on the bonded materials as described in the method below.

If the product is not pre-engaged, the materials are cut from the product and sample preparation would be similar to the method presented above for a sample in a film form.

Refastened samples—Any of the above mentioned bonded samples (e.g., materials in a discrete film form after accelerated aging or material in a product) may be refastened. A refastened sample is prepared as follows. A bonded sample 1010 is manually debonded by peeling the receiving sample 1012 from the engaging sample 1022. The adherent 1024 and adherend 1014 are refastened in a configuration substantially similar to the configuration in which they were originally attached while avoiding wrinkles. The bonded sample is rolled with a 4.5 pound (2 kg) HR-100 ASTM 80 shore rubber-faced roller. Two full strokes (i.e., back and forth) are applied to the sample at a speed of approximately 5 mm/sec. The refastened sample is allowed to sit for 1 minute of dwell time. Debonding and refastening may be repeated to yield a second refastening, third refastening, etc. The refastened sample may be tested to provide a Shear Hang Time.

Test Conditions—The bonded sample 1010 is prepared at ambient room conditions (e.g., 22° C.+/−2° C. and RH 50%+/−10%). The bonded sample 1010 is brought into a temperature chamber immediately prior to the commencement of testing. The time between introduction of the bonded sample 1010 into the temperature chamber and commencement of testing is to be less than 5 minutes. The test is conducted in a 100° F. controlled temperature chamber or oven (37.5° C.±2° C.). Suitable instruments for this test are the RT10 or RT30 available from ChemInstruments Inc, Fairfield, Ohio or any apparatus having a rack or jig capable of holding a test plate within 0° to 2° of vertical. The time is measured by an automated timer capable of reading to the nearest minute.

Figure 10C:
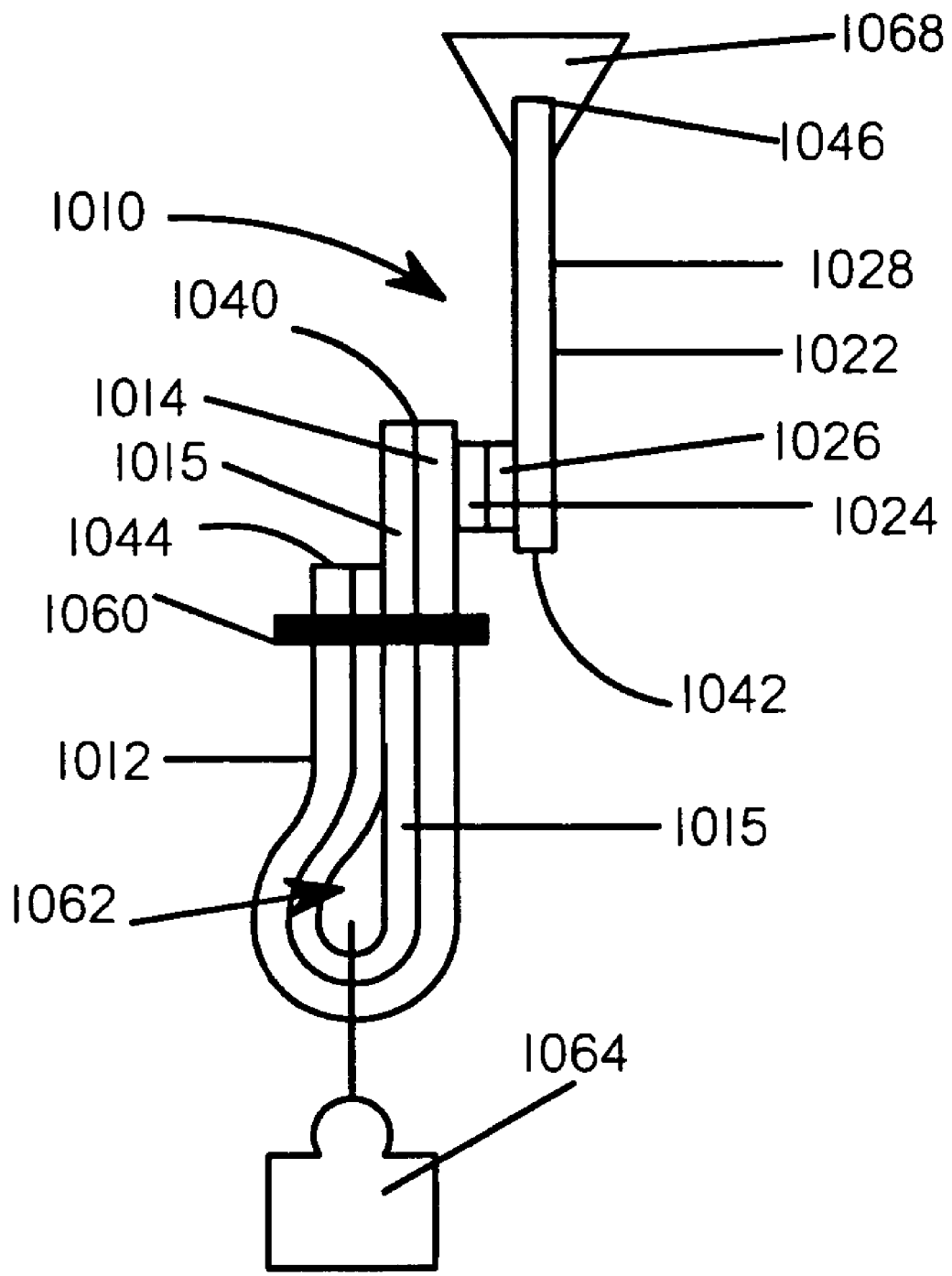
FIG. 10C is sectional view of the sample of FIG. 10C is a test apparatus.

FIG. 10C is a cross-sectional view of the bonded sample 1010 in a test apparatus. The distal edge 1044 of the adherend receiving sample 1012 is folded onto itself and affixed with a staple 1060 to form a loop 1062. The distal edge 1046 of the engaging sample 1022 is placed into the rack 1068 so that the receiving sample 1012 hangs downwards. A 1 kg weight 1064 is attached to the free end of the receiving sample 1012 and may be hooked or engaged through the loop 1062 formed in the adherend 1014. The timer is started once the weight 1064 hangs freely from the receiving sample 1012. The time required for debonding of the adherend 1014 and the adherent 1024 is recorded (i.e., the receiving member 1012 separates and falls from the engaging member 1022). The test can be manually stopped if the sample remains bonded beyond a prescribed time period.

If the bonded sample fails at a time less than specified with this disclosure for some reason other than separation of the interface between the engaging sample and the receiving sample (e.g., the engaging sample tears, receiving sample tears, or the sample debonds at an interface other than of that between the engaging sample and the receiving sample), the data is discarded and another sample must be run using a backing material to prevent the sample from tearing and/or using a stronger double sided tape to prevent separation at interfaces other than between the engaging sample and the receiving sample.

Probe Tack Test Method

Figure 11:
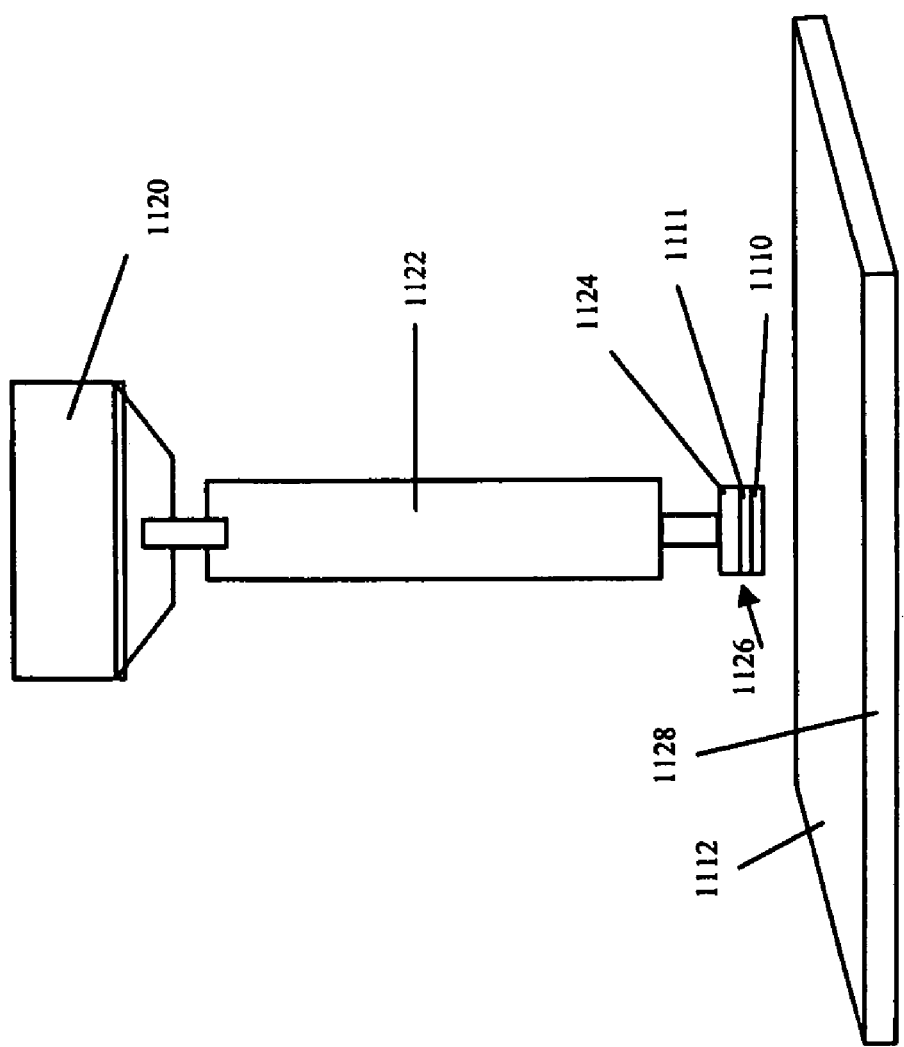
FIG. 11 depicts suitable sample and instrument configuration for the Probe Tack Test.

This method is used to determine the tackiness of select adherents and adherends when placed in contact with a standard surface at a controlled rate and pressure. This test is derived from ASTM D Test Method No. 2979-01 which is directed to Pressure Sensitive Adhesives. FIG. 11 depicts a suitable sample and instrument configuration.

Sample Preparation—For the Instron 5564 instrument listed above, the sample is prepared as follows. The sample material 1110 is bonded to a piece double sided tape 1111 (such as FT 239 available from Avery Denninson Corp., Painesville, Ohio). The sample material 1110/double sided tape 1111 is resized to 1"×1" (approx. 2.5×2.5 cm). The opposite side of the double sided tape 1111 is bonded to the anvil face 1126 of a probe anvil 1124. The sample material 1110/double sided tape 1111 is cut with a knife to fit to the anvil face 1126. The sample material 1110/double sided tape 1111 is to be cut without contaminating or touching the surface of the sample material 1110 that is to be tested. The surface area of the sample material 1110 is approximately the same as the anvil face 1126. If the sample material 1110 is engaged with another material, the sample material 1110 is to be separated from the other material prior to testing. The adherent and adherend are tested.

Test Conditions—The Probe Tack Test is performed in a controlled room at 22° C.+/−2° C. and RH 50%+/−10%. Suitable instruments for this test include tensile testers commercially available from Instron Engineering Corp., Canton, Mass. (e.g. Instron 5564) or equivalent tensile testers.

The instrument is interfaced with a computer which controls the testing parameters, performs data acquisition and calculation, and provides graphs and data reports. The probe anvil 1124 is mounted to a probe body 1122 which is connected to a load cell 1120. The probe anvil 1124 is cylindrical is shape and has a substantially circular anvil face 1126. The anvil face 1126 has a diameter of approximately 1.1 cm and a surface area of 0.95 cm². The load cell 1120 is selected so that the forces to be measured will be between 10% and 90% of the capacity of the load cell 1120. The bottom stationary side of the Instron is mounted with a fixed planar plate 1128 with a predominate surface parallel to the anvil face 1126. The plate 1128 is made from a material that will exhibit a negligible degree of deformation or compression during the test (e.g., a steel plate). A standard surface 1112 is joined to the plate 1128. For purposes of this test method, the standard surface 1112 is a mimic skin available from IMS, Inc., Milford, Conn. as VITROSKIN™ N19. Before testing, the mimic skin is conditioned according to the supplier's instruction. The mimic skin is bonded to the plate 1128 to maintain the mimic skin a substantially planar configuration during testing.

Before measurement, the load reading on the instrument is zeroed to account for the mass of the probe. The anvil face 1126 along with the sample material 1110 are brought into contact with the standard surface 1112 at speed of 1 mm/min until a compression load of 95 gram-force (i.e., corresponding to 9.79 kPa, for a probe of 1.1 cm diameter) is achieved. After a 1 second delay while maintaining the 95 grams force, the probe is pulled away from the standard surface at speed of 10 mm/min. The Maximum Load is then recorded as gram-force. The maximum load is normalized per area of the anvil face: normalized Maximum load=measured maximum load÷anvil face surface area.

Low surface adhesion (i.e., non-tacky) is quantified as a measurement of less than 50 grams force (gf) according to the Probe Tack Test Method. In certain embodiments, low surface adhesion may be less than 40 gf; alternately, less than 30 gf; alternately, less than 20 gf; alternately, less than 10 gf; or alternately, less than 5 gf. Kraton® D1102 and Kraton® D1111 available from Kraton Polymers, Houston, Tex., exhibit a probe tack force of about 2 gf. Vector® 4211 available from Dexco Polymers, Houston, Tex., exhibits a probe tack force of about 2 gf. By way of comparison, Krayton® D1107 available from Kraton Polymers, Houston, Tex., exhibits a probe tack force of about 168 gf.

EXAMPLES

Samples of the materials listed below are tested according to the T-Peel Test Method. The samples are aged for 6 hours, 3 days, and/or 1 week and at a temperature of 60° C. and under 0.8 N/cm² pressure. The T-Peel force is an average from at least 3 samples and is normalized to units of Newtons per inch of initial sample width. Table 1 provides the combinations tested as the adherent and the adherend. The materials tested are referenced by the acronyms provided.

D1102: Kraton® D1102 is available from Kraton Polymers, Houston, Tex. D1102 is a styrene/butadiene/styrene triblock elastomer (16% diblock and 28% styrene). D1102 is extruded to form about a 2-5 mil thick film.

D1111: Kraton® D1111 is available from Kraton Polymers, Houston, Tex. D1111 is a styrene/isoprene/styrene triblock elastomer (15% diblock and 22% styrene). D1111 is extruded to form about a 2-5 mil thick film.

4211: Vectors 4211 is available from Dexco Polymers LP, Houston, Tex. 4211 is a styrene/isoprene/styrene triblock elastomer (0% diblock and 20% styrene). 4211 is extruded to form about a 2-5 mil thick film.

8508: Vector® 8505 is available from Dexco Polymers LP, Houston, Tex. 8505 is a styrene/butadiene/styrene triblock elastomer (0% diblock and 29% styrene). 8508 is extruded to form about a 2-5 mil thick film.

PET: PET is a corona treated, bi-axial oriented poly(ethylene terephthalate) available under tradename Hostanphan® RNK-C from Mitsubishi Polyester Film Gmbh, Wiesbaden, Germany. The PET is supplied as a 12 microns thick film.

oPA54: oPA54 is a bi-oriented polyamide film having a supplier reported surface energy of 54 mN/m. The bi-oriented polyamide 54 is 15 microns thick and is available from CFP Flexible Packaging S.p.A., Italy, under the tradename of Emblem™ 1500.

oPA 40: oPA40 is bi-oriented polyamide film having a supplier reported surface energy of 40 mN/m. The bi-oriented polyamide 40 is the untreated side of the oPA54 Emblem™ film. oPA40 is supplied as a film 15 microns thick.

PE50: PE50 is the corona treated side of a polyethylene film manufactured by Nordenia International AG as supplier code KC 2672.770. PE50 has a thickness of 95 microns and a supplier reported surface energy of 50 mN/m. PE50 has a density of 0.93 g/cm³.

PE33: PE33 is the untreated side of the PE50 polyethylene film manufactured by Nordenia International AG. PE33 has a supplier reported surface energy of 33 mN/m.

PP44: PP44 is the corona treated side of a polypropylene film having a supplier reported surface energy of 44 mN/m available as supplier code 14461 from Huhtamaki Forchheim GmbH, Germany. PP44 has a thickness of 70 microns and a density of 0.9 g/cm³.

PP33: PP33 is the untreated side of the PP44 polypropylene film manufactured by Huhtamaki Forchheim GmbH, Germany. PP33 has a surface energy of 33 mN/m.

oPP42: oPP42 is a bi-oriented polypropylene film double coated with acrylic and is manufactured by ExxonMobil Inc., Luxembourg under the trade name MW 647 OPPalyte™. oPP42 has a supplier reported surface energy of 42 mN/m and a thickness of 40 microns.

TABLE 1

| Adherend | Adherent | | | |
|---|---|---|---|---|
| | D1102 | D1111 | 4211 | 8508 |
| PET | 6.5 ± 0.2 (6 h) | 2.6 ± 0.5 (6 h) | 8.0 ± 0.1 (6 h) | 5.4 ± 0.9 (6 h) |
| | 8.0 ± 0.2 (3 d) | 6.0 ± 0.02 (3 d) | 13.6 ± 3 (3 d) | 8.2 ± 0.2 (3 d) |
| | 8.0 ± 0.6 (1 w) | 9.0 ± 0.2 (1 w) | 16 ± 4 (1 w) | |
| oPA54 | 5.0 ± 0.5 (6 h) | 4.4 ± 1.9 (6 h) | 4.2 ± 0 (6 h) | |
| | 4.9 ± 0.5 (3 d) | 6.0 ± 0.6 (3 d) | Lock Up (3 d) | |
| | 5.8 ± 0.4 (1 w) | 8.0 ± 5.0 (1 w) | | |
| oPA40 | 3.1 ± 0.1 (6 h) | 1.9 ± 1.0 (6 h) | 3.6 ± 0.2 (6 h) | |
| | 4.3 ± 0.3 (3 d) | 6.6 ± 0.7 (3 d) | 6.0 ± 0.9 (3 d) | |
| | 5.1 ± 0.3 (1 w) | | 5.8 ± 1.3 (1 w) | |
| PE50 | 11.9 ± 0.3 (6 h) | 3.1 ± 2.4 (6 h) | 6.9 ± 0.6 (6 h) | |
| | 11.0 ± 1.0 (3 d) | 9.0 ± 0.6 (3 d) | Lock Up (3 d) | |
| PE33 | 2.2 ± 0.1 (6 h) | 0.5 ± 0.7 (6 h) | 0.5 ± 0.2 (6 h) | |
| | 2.2 ± 0.0 (3 d) | 8.0 ± 0.9 (3 d) | 1.5 ± 0.2 (3 d) | |
| PP33 | 8.9 ± 0.1 (6 h) | 3.0 ± 3.0 (6 h) | 7.3 ± 0.7 (6 h) | |
| | 12.0 ± 0.3 (3 d) | 9.4 ± 0.6 (3 d) | 12.5 ± 0.3 (3 d) | |
| PP44 | 9.0 ± 0.3 (6 h) | 5.4 ± 1.6 (6 h) | 8.5 ± 0.8 (6 h) | |
| | 13.6 ± 0.1 (3 d) | 14.0 ± 2.0 (3 d) | Lock Up (3 d) | |
| | | 17.0 ± 5.0 (1 w) | | |
| oPP42 | Lock Up (6 h) | 4.4 ± 0.9 (6 h) | Lock Up (6 h) | |
| | | 8.0 ± 1.0 (3 d) | | |
| D1111 | | 4.7 ± 0.5 (6 h) | | |
| | | 10.7 ± 0.7 (3 d) | | |
| | | 17.0 ± 1.0 (1 w) | | |
| 4211 | | | Lock Up (6 h) | |
| 8508 | | | | Lock Up (6 h) |

All values are in N/inch.
6 h = 6 hours of accelerated aging.
3 d = 3 days of accelerated aging.
1 w = 1 week of accelerated aging.

Example 1

Example 1 comprises an adherent of D1102 and an adherend of PET. The Kraton D1102 is supplied as pellets. Kraton D1102 is extruded into about a 3 mil thick film. D1102 is a styrenelbutadiene/styrene triblock elastomer having 16% diblock, and 28% styrene. The weight average molecular weight of the D1102 was determined to be 71 kDa (molecular weight is determined by gel permeation chromatography using polystyrene standards in tetrahydrofuran). D1102 has a supplier reported melt flow rate of 6 g/10 min (as measured by International Organization for Standardization method ISO 1133 at the conditions of 200° C./5 kg).

Example 2

Example 2 comprises an adherent of D1102 (as described in Example 1 above) and a adherend of oPA 54.

Example 3

Example 3 comprises an adherent of D1102 (as described in Example 1 above) and a adherend of oPA 40.

Example 4

Example 4 comprises an adherent of 4211 and an adherend of oPA40 (as described in Example 3 above). Vector 4211 is supplied as pellets. Vector 4211 is extruded into about a 3 mil thick film. The weight average molecular weight of the 4211 was determined to be 86 kDa (molecular weight is determined by gel permeation chromatography using polystyrene standards in tetrahydrofuran). 4211 has a supplier reported melt flow rate of 12 g/10 min (as measured ASTM method D 1238 at the test conditions of 200° C./5 kg).

Test Results

Figure 12:
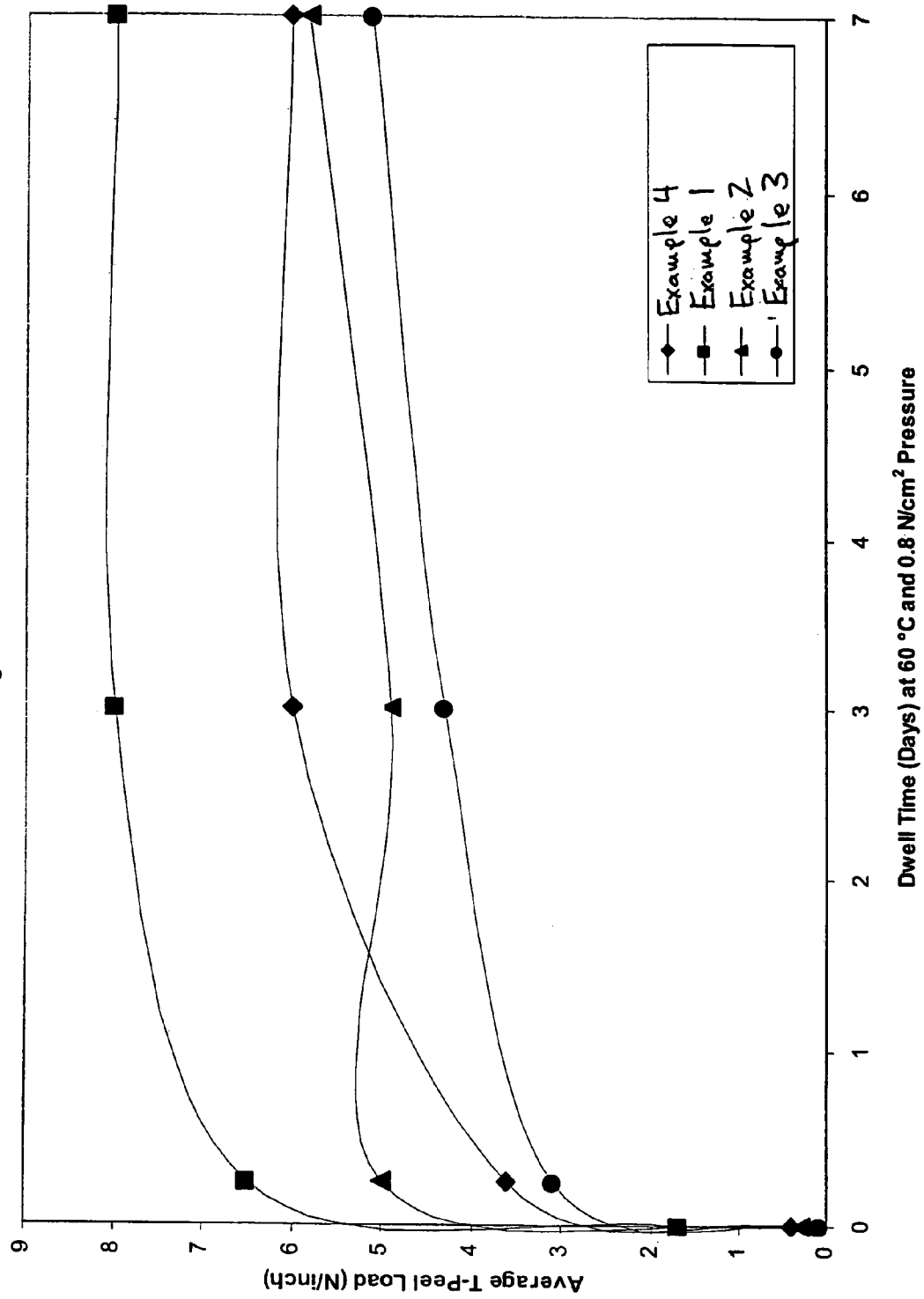
FIG. 12 is a graph showing T-Peel force plotted against time of aging.

Table 2 provides the T-Peel test results for Examples 1-4 subjected to aging for either 6 hours, 3 days, or 1 week and at a temperature of 60° C. under 0.8 N/cm$^2$ pressure. The T-Peel force is an average from at least 3 samples. FIG. 11 shows a plot of these T-Peel values versus time. As can be seen from Table 2 and FIG. 12, the T-Peel force plateaus over time. The T-Peel force after 1 week of aging does is not appreciably greater than the T-Peel force measured after 3 days of aging. The data shows less than about a 20% increase in T-Peel force from 3 days of aging to 1 week of aging.

TABLE 2

| Sample | T-Peel (N/inch) after 6 hours at 60° C. | T-Peel (N/inch) after 3 days at 60° C. | T-Peel (N/inch) after 1 week at 60° C. |
|---|---|---|---|
| Example 1 | 6.5 ± 0.2 | 8.0 ± 0.2 | 8.0 ± 0.6 |
| Example 2 | 5.0 ± 0.5 | 4.9 ± 0.5 | 5.8 ± 0.4 |
| Example 3 | 3.1 ± 0.1 | 4.3 ± 0.3 | 5.1 ± 0.3 |
| Example 4 | 3.6 ± 0.2 | 6.0 ± 0.9 | 5.8 ± 1.3 |

Table 3 provides the T-Peel test results for Examples 1-4 subjected to 1 week of aging at a temperature of 60° C. and one or more refastening events (1, 2, or 3 times with a 1 minute dwell time after refastening). As can be appreciated, the T-Peel force does not appreciably degrade over the refastening events. The T-Peel force of a sample after 3 refastening events is no more than about 1 N/inch less than the T-Peel force for the same sample after 1 refastening event.

TABLE 3

| Sample | T-Peel (N/inch) after 1 week at 60° C. 1st refastening | T-Peel (N/inch) after 1 week at 60° C. 2nd refastening | T-Peel (N/inch) after 1 week at 60° C. 3rd refastening |
| --- | --- | --- | --- |
| Example 1 | 3.8 ± 0.3 | 3.6 ± 0.3 | 3.4 ± 0.2 |
| Example 2 | 4.1 ± 0.4 | 4.0 ± 0.2 | 3.8 ± 0.2 |
| Example 3 | 3.7 ± 0.3 | 3.6 ± 0.3 | 3.4 ± 0.2 |
| Example 4 | 4.3 ± 0.5 | 4.2 ± 0.6 | 4.2 ± 0.6 |

Table 4 provides the Dynamic Shear test results for Examples 1-4 subjected to aging for 1 week or 3 days at a temperature of 60° C. Table 4 also provides the Dynamic Shear for Examples 1-4 after three refastening events.

TABLE 4

| Sample | Dynamic shear (N/inch$^2$) after 1 week at 60° C. prior to refastening | Dynamic shear (N/inch$^2$) after 1 week at 60° C. and 3 refastening events |
| --- | --- | --- |
| Example 1 | 94 ± 13* | 89 ± 11* |
| Example 2 | 87 ± 2* | 98 ± 2* |
| Example 3 | 78 ± 7* | 66 ± 5* |
| Example 4 | 66 ± 7* | 67 ± 6* |

| Sample | Dynamic shear (N/inch$^2$) after 3 days at 60° C. prior to refastening | Dynamic shear (N/inch$^2$) after 3 days at 60° C. and 3 refastening events |
| --- | --- | --- |
| Example 4 | 129 ± 5* | 119 ± 6 |

*The dynamic shear values are due to the failure of the adherend film.

Table 5 provides the Shear Hang Time test results for Examples 1-4 subjected to 3 days of aging at a temperature of 60° C. Table 5 also provides the Shear Hang Time test results for Examples 1-4 subjected to 3 days of aging at a temperature of 60° C. and three refastening events. A value of "pass" indicates that the Example remains attached for at least 240 minutes.

TABLE 5

| Sample | 240 minutes of Shear hang time after 3 days at 60° C. | 240 minutes of Shear hang time after 3 days at 60° C. and three refastening events |
| --- | --- | --- |
| Example 1 | Pass | Pass |
| Example 2 | Pass | Pass |
| Example 3 | Pass | Pass |
| Example 4 | Pass | Pass |

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising
   a) an absorbent assembly comprising:
      i) a liquid permeable topsheet,
      ii) a backsheet, and
      iii) an absorbent core disposed therebetween,
   wherein the absorbent assembly has a front waist region, a rear waist region and a crotch region between and connecting the front and rear waist regions;
   b) a pair of side panels, each side panel comprising a front side panel disposed transversely from the front waist region and a rear side panel disposed transversely from the rear waist region;
   c) a pre-engaged non-tacky adhesive fastening system comprising a non-tacky, non-mechanical, adhesive adherent and a non-tacky, non-mechanical, adhesive adherend,
   wherein the non-tacky, non-mechanical, adhesive adherent and the non-tacky, non-mechanical, adhesive adherend are pre-engaged to join the front side panel and rear side panel; the pre-engaged non-tacky adhesive fastening system, after aging, exhibits a T-Peel of from about 1N/inch to about 12N/inch; the pre-engaged non-tacky adhesive fastening system is refastenable; the non-tacky, non-mechanical, adhesive adherent and the non-tacky, non-mechanical, adhesive adherend are selected from the group consisting of selective adhesives, cohesives, and combinations thereof; and the non-tacky, non-mechanical, adhesive adherent and the non-tacky, non-mechanical adhesive adherent exhibit a probe tack force of less than 50 grams force; and
   d) a tab and slot fastening system comprising a first member and a second member, wherein the first member is joined to the front side panel and the second member is joined to the rear side panel;
   wherein the non-tacky, non-mechanical, adhesive adherent is disposed on the first member and the non-tacky, non-mechanical, adhesive adherend is disposed on the second member, and the absorbent article is manufactured with the tab and slot fastening system in an unfastened state.

2. The absorbent article of claim 1 wherein the first member of the tab and slot fastening system is a tab member.

3. The absorbent article of claim 1 wherein the first and second members of the tab and slot fastening system are flexible.

4. The absorbent article of claim 1 wherein the first and second members of the tab and slot fastening system are discrete elements joined to the absorbent article.

5. The absorbent article of claim 1 wherein the first and second members of the tab and slot fastening system can be joined in a face-to-face relationship.

6. The absorbent article of claim 1 wherein the first and second members of the tab and slot fastening system can be joined by inserting a tab member through a slot member.

* * * * *

UNITED STATES PATENT AND TRADEMARK OFFICE
CERTIFICATE OF CORRECTION

| | | |
|---|---|---|
| PATENT NO. | : 7,722,592 B2 | Page 1 of 1 |
| APPLICATION NO. | : 11/324486 | |
| DATED | : May 25, 2010 | |
| INVENTOR(S) | : Urmish Popatlal Dalal et al. | |

It is certified that error appears in the above-identified patent and that said Letters Patent is hereby corrected as shown below:

Column 11

Line 20, delete "IN/inch" and insert -- 1N/inch --.

Column 33

Line 37, delete "styrenelbutadiene/styrene" and insert -- styrene/butadiene/styrene --.

Signed and Sealed this

Eighth Day of February, 2011

David J. Kappos
*Director of the United States Patent and Trademark Office*